(12) United States Patent
Bruce et al.

(10) Patent No.: US 9,957,311 B2
(45) Date of Patent: May 1, 2018

(54) SURFACE-BINDING PEPTIDE

(71) Applicant: TIKOMED AB, Viken (SE)

(72) Inventors: Lars Bruce, Viken (SE); Staale Lyngstadaas, Nesoddtangen (NO)

(73) Assignee: TIKOMED AB, Viken (SE)

( * ) Notice: Subject to any disclaimer, the term of this patent is extended or adjusted under 35 U.S.C. 154(b) by 0 days. days.

(21) Appl. No.: 15/106,190

(22) PCT Filed: Dec. 19, 2014

(86) PCT No.: PCT/SE2014/051543
§ 371 (c)(1),
(2) Date: Jun. 17, 2016

(87) PCT Pub. No.: WO2015/094111
PCT Pub. Date: Jun. 25, 2015

(65) Prior Publication Data
US 2016/0368959 A1  Dec. 22, 2016

(30) Foreign Application Priority Data

Dec. 20, 2013  (SE) ........................................ 1351541

(51) Int. Cl.

| | |
|---|---|
| *C07K 14/57* | (2006.01) |
| *A61L 27/54* | (2006.01) |
| *A61L 27/04* | (2006.01) |
| *A61L 27/06* | (2006.01) |
| *A61L 27/28* | (2006.01) |
| *A61L 27/50* | (2006.01) |
| *C07K 14/52* | (2006.01) |
| *C07K 5/11* | (2006.01) |
| *C07K 5/103* | (2006.01) |

(52) U.S. Cl.
CPC .............. *C07K 14/57* (2013.01); *A61L 27/04* (2013.01); *A61L 27/047* (2013.01); *A61L 27/06* (2013.01); *A61L 27/28* (2013.01); *A61L 27/50* (2013.01); *A61L 27/54* (2013.01); *C07K 14/522* (2013.01); *A61L 2300/25* (2013.01); *A61L 2400/18* (2013.01); *C07K 5/1013* (2013.01); *C07K 5/1019* (2013.01); *C07K 2319/00* (2013.01)

(58) Field of Classification Search
CPC .... C07K 14/57; C07K 14/522; C07K 5/1019; C07K 5/1013; C07K 2319/00; A61L 27/04; A61L 27/50; A61L 27/54; A61L 27/047; A61L 27/06; A61L 27/28; A61L 2300/25; A61L 2400/18
See application file for complete search history.

(56) References Cited

U.S. PATENT DOCUMENTS

2008/0027005 A1  1/2008  Averback et al.

FOREIGN PATENT DOCUMENTS

| WO | 2008/033069 A1 | 3/2008 | |
|---|---|---|---|
| WO | 2008/085828 A2 | 7/2008 | |
| WO | 2009/092062 A2 | 7/2009 | |
| WO | 2010/063124 A1 | 6/2010 | |
| WO | 2010/065594 A2 | 6/2010 | |
| WO | WO 2011/119484 A1 * | 9/2011 | ............ G06F 19/18 |
| WO | 2013/055749 A1 | 4/2013 | |

OTHER PUBLICATIONS

Guo et al, A novel fusion protein of IP10-scFv retains antibody specificity and chemokine function, Biochemical and Biophysical Research Communications, 2004, 320, pp. 506-513.*
Mouse IP-10 sequence, from http://www.uniprot.org/uniprot/P17515, pp. 1-9, accessed Mar. 7, 2017.*
Campanella et al, CXCR3 and Heparin Binding Sites of the Chemokine IP-10 (CXCL10), The Journal of Biological Chemistry, 2003, 278, pp. 17066-17074.*
Putative tRNA-splicing ligase RtcB, from https://www.ncbi.nlm.nih.gov/protein/948276122?report=genbank&log$=protalign&blast_rank=1&RID=M5UDVBG3015, pp. 1-2, accessed Jun. 15, 2017.*
Sequence for WO2011119484 A1, from http://segdata.uspto.gov/?pageRequest=viewSequence&DocID=US20130330335A1&seqID=137365%2C175305%2C388249, p. 1, accessed Jun. 20, 2017.*
Site-specific AF647® Labelled Chemokines-Almac, from https://www.almacgroup.com/site-specific-af647-labelled-chemokines/, Jun. 7, 2012, pp. 1-5.*
BD-Flow-Cytom-Learning-Guide, Dec. 2002, pp. 1-58.*
Cole et al, Cutting Edge: IFN-Inducible ELR- CXC Chemokines Display Defensin-Like Antimicrobial Activity, The Journal of Immunology, 2001, 167, pp. 623-627.*
Shintani, Modification of Medical Device Surface to attain Anti-Infection, Trends Biomater. Artif. Organs, 2004, 18, pp. 1-8.*
Valerie Booth et al., The CXCR3 Binding Chemokine IP-10/CXCL10: Structure and Receptor Interactions, Biochemistry, 41:10418-10425 (published online Jul. 23, 2002).

* cited by examiner

*Primary Examiner* — Julie Ha
*Assistant Examiner* — Li N Komatsu
(74) *Attorney, Agent, or Firm* — Porter Wright Morris & Arthur LLP

(57) ABSTRACT

Surface-binding peptides have the capability of binding to surfaces of biocompatible materials and can thereby be used to immobilize various heterologous molecules of interest onto the surface. This means that surfaces of, for instance, implants and implantable medical devices can be tailored to present various characteristics by immobilizing selected heterologous molecules of interest on the surfaces of the implants and implantable medical devices. The surface-binding peptides consist of 5-17 consecutive amino acids of an extended beta-hairpin motif EIIATMKKKGEKRCLNP (SEQ ID NO: 57) in Interferon gamma-induced protein 10 (IP-10).

22 Claims, 14 Drawing Sheets

```
VPLSRTVRCTCISISNQPVNPRSLEKLEIIPASQFCPRVEIIATMKKKGEKRCLNPESKAIKNLLKAVSKERSKRSP    IP-10                  (SEQ ID NO: 18)
VPLSRTVRCTCISISNQPVN                                                             PEPTIDE 1              (SEQ ID NO: 1)
       CISISNQPVNPRSLEKLEII                                                      PEPTIDE 2              (SEQ ID NO: 2)
                PRSLEKLEIIPASQFCPRVE                                             PEPTIDE 3              (SEQ ID NO: 3)
                         PASQFCPRVEIIATMKKKGE                                    PEPTIDE 4              (SEQ ID NO: 4)
                                  IIATMKKKGEKRCLNPESKA                           PEPTIDE 5              (SEQ ID NO: 5)
                                            IKNLLKAVSKERSKRSP                    PEPTIDE 6              (SEQ ID NO: 6)
                                              KAIKNLLKA                          PEPTIDE 7              (SEQ ID NO: 7)
   CTCISISNQPVNPRSLEKLEIIPASQFC                                                  PEPTIDE 8              (SEQ ID NO: 8)
                          FCPRVEPASQ                                             PEPTIDE 9              (SEQ ID NO: 9)
                    EPASQFCPRV                                                   PEPTIDE 10             (SEQ ID NO: 10)
                          FCPRVEIIAT                                             PEPTIDE 11             (SEQ ID NO: 11)
                                    MKKKGEIIAT                                   PEPTIDE 12             (SEQ ID NO: 12)
                                  EIIATMKKKG                                     PEPTIDE 13             (SEQ ID NO: 13)
                         PASQFCPRVE                                              PEPTIDE 14             (SEQ ID NO: 14)
                                  EIIATMKKKGE                                    PEPTIDE 15             (SEQ ID NO: 15)
                             CPRVEIIATM                                          PEPTIDE 16             (SEQ ID NO: 16)
                           SQFCPRVEIIATMKKK                                      PEPTIDE 17             (SEQ ID NO: 17)
```

Fig. 2

SEQUENCE LISTING

<160> NUMBER OF SEQ ID NOS: 69

<210> SEQ ID NO 1
<211> LENGTH: 20
<212> TYPE: PRT
<213> ORGANISM: Homo sapiens

<400> SEQUENCE: 1

Val Pro Leu Ser Arg Thr Val Arg Cys Thr Cys Ile Ser Ile Ser Asn
1               5                   10                  15

Gln Pro Val Asn
            20

<210> SEQ ID NO 2
<211> LENGTH: 20
<212> TYPE: PRT
<213> ORGANISM: Homo sapiens

```
<400> SEQUENCE: 2

Cys Ile Ser Ile Ser Asn Gln Pro Val Asn Pro Arg Ser Leu Glu Lys
1               5                   10                  15

Leu Glu Ile Ile
            20

<210> SEQ ID NO 3
<211> LENGTH: 20
<212> TYPE: PRT
<213> ORGANISM: Homo sapiens

<400> SEQUENCE: 3

Pro Arg Ser Leu Glu Lys Leu Glu Ile Ile Pro Ala Ser Gln Phe Cys
1               5                   10                  15

Pro Arg Val Glu
            20

<210> SEQ ID NO 4
<211> LENGTH: 20
<212> TYPE: PRT
<213> ORGANISM: Homo sapiens

<400> SEQUENCE: 4

Pro Ala Ser Gln Phe Cys Pro Arg Val Glu Ile Ile Ala Thr Met Lys
1               5                   10                  15

Lys Lys Gly Glu
            20

<210> SEQ ID NO 5
<211> LENGTH: 20
<212> TYPE: PRT
<213> ORGANISM: Homo sapiens

<400> SEQUENCE: 5

Ile Ile Ala Thr Met Lys Lys Lys Gly Glu Lys Arg Cys Leu Asn Pro
1               5                   10                  15

Glu Ser Lys Ala
            20

<210> SEQ ID NO 6
<211> LENGTH: 17
<212> TYPE: PRT
<213> ORGANISM: Homo sapiens

<400> SEQUENCE: 6

Ile Lys Asn Leu Leu Lys Ala Val Ser Lys Glu Arg Ser Lys Arg Ser
1               5                   10                  15

Pro

<210> SEQ ID NO 7
<211> LENGTH: 9
<212> TYPE: PRT
<213> ORGANISM: Homo sapiens

<400> SEQUENCE: 7

Lys Ala Ile Lys Asn Leu Leu Lys Ala
1               5

<210> SEQ ID NO 8
<211> LENGTH: 28
<212> TYPE: PRT
```

```
<213> ORGANISM: Homo sapiens

<400> SEQUENCE: 8

Cys Thr Cys Ile Ser Ile Ser Asn Gln Pro Val Asn Pro Arg Ser Leu
1               5                   10                  15

Glu Lys Leu Glu Ile Ile Pro Ala Ser Gln Phe Cys
            20                  25

<210> SEQ ID NO 9
<211> LENGTH: 10
<212> TYPE: PRT
<213> ORGANISM: Artificial Sequence
<220> FEATURE:
<223> OTHER INFORMATION: IP-10 derived peptide

<400> SEQUENCE: 9

Phe Cys Pro Arg Val Glu Pro Ala Ser Gln
1               5                   10

<210> SEQ ID NO 10
<211> LENGTH: 10
<212> TYPE: PRT
<213> ORGANISM: Artificial Sequence
<220> FEATURE:
<223> OTHER INFORMATION: IP-10 derived peptide

<400> SEQUENCE: 10

Glu Pro Ala Ser Gln Phe Cys Pro Arg Val
1               5                   10

<210> SEQ ID NO 11
<211> LENGTH: 10
<212> TYPE: PRT
<213> ORGANISM: Homo sapiens

<400> SEQUENCE: 11

Phe Cys Pro Arg Val Glu Ile Ile Ala Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: IP-10 derived peptide

<400> SEQUENCE: 12

Met Lys Lys Lys Gly Glu Ile Ile Ala Thr
1               5                   10

<210> SEQ ID NO 13
<211> LENGTH: 10
<212> TYPE: PRT
<213> ORGANISM: Homo sapiens

<400> SEQUENCE: 13

Glu Ile Ile Ala Thr Met Lys Lys Lys Gly
1               5                   10

<210> SEQ ID NO 14
<211> LENGTH: 10
<212> TYPE: PRT
<213> ORGANISM: Homo sapiens

<400> SEQUENCE: 14
```

```
Pro Ala Ser Gln Phe Cys Pro Arg Val Glu
1               5                   10
```

<210> SEQ ID NO 15
<211> LENGTH: 11
<212> TYPE: PRT
<213> ORGANISM: Homo sapiens

<400> SEQUENCE: 15

```
Glu Ile Ile Ala Thr Met Lys Lys Lys Gly Glu
1               5                   10
```

<210> SEQ ID NO 16
<211> LENGTH: 10
<212> TYPE: PRT
<213> ORGANISM: Homo sapiens

<400> SEQUENCE: 16

```
Cys Pro Arg Val Glu Ile Ile Ala Thr Met
1               5                   10
```

<210> SEQ ID NO 17
<211> LENGTH: 16
<212> TYPE: PRT
<213> ORGANISM: Homo sapiens

<400> SEQUENCE: 17

```
Ser Gln Phe Cys Pro Arg Val Glu Ile Ile Ala Thr Met Lys Lys Lys
1               5                   10                  15
```

<210> SEQ ID NO 18
<211> LENGTH: 77
<212> TYPE: PRT
<213> ORGANISM: Homo sapiens

<400> SEQUENCE: 18

```
Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
                20                  25                  30

Ser Gln Phe Cys Pro Arg Val Glu Ile Ile Ala Thr Met Lys Lys Lys
            35                  40                  45

Gly Glu Lys Arg Cys Leu Asn Pro Glu Ser Lys Ala Ile Lys Asn Leu
        50                  55                  60

Leu Lys Ala Val Ser Lys Glu Arg Ser Lys Arg Ser Pro
65                  70                  75
```

<210> SEQ ID NO 19
<211> LENGTH: 14
<212> TYPE: PRT
<213> ORGANISM: Homo sapiens

<400> SEQUENCE: 19

```
Glu Ile Ile Ala Thr Met Lys Lys Lys Gly Glu Lys Arg Cys
1               5                   10
```

<210> SEQ ID NO 20
<211> LENGTH: 5
<212> TYPE: PRT
<213> ORGANISM: Homo sapiens

<400> SEQUENCE: 20

```
Ala Thr Met Lys Lys
1               5
```

```
<210> SEQ ID NO 21
<211> LENGTH: 5
<212> TYPE: PRT
<213> ORGANISM: Homo sapiens

<400> SEQUENCE: 21

Thr Met Lys Lys Lys
1               5

<210> SEQ ID NO 22
<211> LENGTH: 5
<212> TYPE: PRT
<213> ORGANISM: Homo sapiens

<400> SEQUENCE: 22

Met Lys Lys Lys Gly
1               5

<210> SEQ ID NO 23
<211> LENGTH: 5
<212> TYPE: PRT
<213> ORGANISM: Homo sapiens

<400> SEQUENCE: 23

Lys Lys Lys Gly Glu
1               5

<210> SEQ ID NO 24
<211> LENGTH: 5
<212> TYPE: PRT
<213> ORGANISM: Artificial Sequence
<220> FEATURE:
<223> OTHER INFORMATION: IP-10 derived peptide

<400> SEQUENCE: 24

Lys Lys Gly Glu Ile
1               5

<210> SEQ ID NO 25
<211> LENGTH: 5
<212> TYPE: PRT
<213> ORGANISM: Artificial Sequence
<220> FEATURE:
<223> OTHER INFORMATION: IP-10 derived peptide

<400> SEQUENCE: 25

Lys Gly Glu Ile Ile
1               5

<210> SEQ ID NO 26
<211> LENGTH: 5
<212> TYPE: PRT
<213> ORGANISM: Artificial Sequence
<220> FEATURE:
<223> OTHER INFORMATION: IP-10 derived peptide

<400> SEQUENCE: 26

Gly Glu Ile Ile Ala
1               5

<210> SEQ ID NO 27
<211> LENGTH: 5
<212> TYPE: PRT
<213> ORGANISM: Homo sapiens
```

```
<400> SEQUENCE: 27

Ile Ala Thr Met Lys
1               5

<210> SEQ ID NO 28
<211> LENGTH: 5
<212> TYPE: PRT
<213> ORGANISM: Homo sapiens

<400> SEQUENCE: 28

Ile Ile Ala Thr Met
1               5

<210> SEQ ID NO 29
<211> LENGTH: 14
<212> TYPE: PRT
<213> ORGANISM: Artificial Sequence
<220> FEATURE:
<223> OTHER INFORMATION: IP-10 derived peptide

<400> SEQUENCE: 29

Ile Ile Ala Thr Met Lys Lys Lys Gly Glu Ile Ile Ala Thr
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Control peptide

<400> SEQUENCE: 30

Lys Lys Lys Lys Lys
1               5

<210> SEQ ID NO 31
<211> LENGTH: 10
<212> TYPE: PRT
<213> ORGANISM: Artificial Sequence
<220> FEATURE:
<223> OTHER INFORMATION: IP-10 derived peptide linked to randomized tag
      sequence

<400> SEQUENCE: 31

Thr Met Lys Lys Lys Pro Glu Ser Cys Phe
1               5                   10

<210> SEQ ID NO 32
<211> LENGTH: 10
<212> TYPE: PRT
<213> ORGANISM: Artificial Sequence
<220> FEATURE:
<223> OTHER INFORMATION: IP-10 derived peptide linked to randomized tag
      sequence

<400> SEQUENCE: 32

Phe Cys Ser Glu Pro Lys Lys Lys Met Thr
1               5                   10

<210> SEQ ID NO 33
<211> LENGTH: 5
<212> TYPE: PRT
<213> ORGANISM: Artificial Sequence
<220> FEATURE:
<223> OTHER INFORMATION: Randomized tag sequence
```

```
<400> SEQUENCE: 33

Pro Glu Ser Cys Phe
1               5

<210> SEQ ID NO 34
<211> LENGTH: 18
<212> TYPE: PRT
<213> ORGANISM: Artificial Sequence
<220> FEATURE:
<223> OTHER INFORMATION: IP-10 derived peptide connected to RGD motif
      via poly-G-linker

<400> SEQUENCE: 34

Met Lys Lys Lys Gly Glu Gly Gly Gly Gly Gly Gly Gly Arg Gly
1               5                   10                  15

Asp Ser

<210> SEQ ID NO 35
<211> LENGTH: 18
<212> TYPE: PRT
<213> ORGANISM: Artificial Sequence
<220> FEATURE:
<223> OTHER INFORMATION: Mutated IP-10 derived peptide connected to RGD
      motif via poly-G-linker

<400> SEQUENCE: 35

Met Thr Thr Thr Gly Glu Gly Gly Gly Gly Gly Gly Gly Arg Gly
1               5                   10                  15

Asp Ser

<210> SEQ ID NO 36
<211> LENGTH: 18
<212> TYPE: PRT
<213> ORGANISM: Artificial Sequence
<220> FEATURE:
<223> OTHER INFORMATION: IP-10 derived peptide connected to mutated RGD
      motif via poly-G-linker

<400> SEQUENCE: 36

Met Lys Lys Lys Gly Glu Gly Gly Gly Gly Gly Gly Gly Arg Gly
1               5                   10                  15

Glu Ser

<210> SEQ ID NO 37
<211> LENGTH: 18
<212> TYPE: PRT
<213> ORGANISM: Artificial Sequence
<220> FEATURE:
<223> OTHER INFORMATION: Mutated IP-10 derived peptide connected to
      mutated RGD motif via poly-G-linker

<400> SEQUENCE: 37

Met Thr Thr Thr Gly Glu Gly Gly Gly Gly Gly Gly Gly Arg Gly
1               5                   10                  15

Glu Ser

<210> SEQ ID NO 38
<211> LENGTH: 20
<212> TYPE: DNA
<213> ORGANISM: Artificial Sequence
<220> FEATURE:
<223> OTHER INFORMATION: Primer for RT-PCR

<400> SEQUENCE: 38
```
gtaacccgtt gaacccatt                                              20

<210> SEQ ID NO 39
<211> LENGTH: 20
<212> TYPE: DNA
<213> ORGANISM: Artificial Sequence
<220> FEATURE:
<223> OTHER INFORMATION: Primer for RT-PCR

<400> SEQUENCE: 39
ccatccaatc ggtagtagcg                                              20

<210> SEQ ID NO 40
<211> LENGTH: 20
<212> TYPE: DNA
<213> ORGANISM: Artificial Sequence
<220> FEATURE:
<223> OTHER INFORMATION: Primer for RT-PCR

<400> SEQUENCE: 40
acccagaaga ctgtggatgg                                              20

<210> SEQ ID NO 41
<211> LENGTH: 20
<212> TYPE: DNA
<213> ORGANISM: Artificial Sequence
<220> FEATURE:
<223> OTHER INFORMATION: Primer for RT-PCR

<400> SEQUENCE: 41
cacattgggg gtaggaacac                                              20

<210> SEQ ID NO 42
<211> LENGTH: 20
<212> TYPE: DNA
<213> ORGANISM: Artificial Sequence
<220> FEATURE:
<223> OTHER INFORMATION: Primer for RT-PCR

<400> SEQUENCE: 42
agagcatgac cgatggattc                                              20

<210> SEQ ID NO 43
<211> LENGTH: 20
<212> TYPE: DNA
<213> ORGANISM: Artificial Sequence
<220> FEATURE:
<223> OTHER INFORMATION: Primer for RT-PCR

<400> SEQUENCE: 43
ccttcttgag gttgccagtc                                              20

<210> SEQ ID NO 44
<211> LENGTH: 20
<212> TYPE: DNA
<213> ORGANISM: Artificial Sequence
<220> FEATURE:
<223> OTHER INFORMATION: Primer for RT-PCR

<400> SEQUENCE: 44
tcgcctggga ggaggcgaaa                                              20

<210> SEQ ID NO 45
<211> LENGTH: 21
<212> TYPE: DNA
<213> ORGANISM: Artificial Sequence -continued

```
<220> FEATURE:
<223> OTHER INFORMATION: Primer for RT-PCR

<400> SEQUENCE: 45
tcttaaccgc tgtgctcccc g                                              21

<210> SEQ ID NO 46
<211> LENGTH: 21
<212> TYPE: DNA
<213> ORGANISM: Artificial Sequence
<220> FEATURE:
<223> OTHER INFORMATION: Primer for RT-PCR

<400> SEQUENCE: 46
aggggagatg tgttccggcc a                                              21

<210> SEQ ID NO 47
<211> LENGTH: 20
<212> TYPE: DNA
<213> ORGANISM: Artificial Sequence
<220> FEATURE:
<223> OTHER INFORMATION: Primer for RT-PCR

<400> SEQUENCE: 47
acacacagct gccgcactcg                                                20

<210> SEQ ID NO 48
<211> LENGTH: 5
<212> TYPE: PRT
<213> ORGANISM: Homo sapiens

<400> SEQUENCE: 48

Lys Lys Gly Glu Lys
1               5

<210> SEQ ID NO 49
<211> LENGTH: 5
<212> TYPE: PRT
<213> ORGANISM: Homo sapiens

<400> SEQUENCE: 49

Lys Gly Glu Lys Arg
1               5

<210> SEQ ID NO 50
<211> LENGTH: 5
<212> TYPE: PRT
<213> ORGANISM: Homo sapiens

<400> SEQUENCE: 50

Gly Glu Lys Arg Cys
1               5

<210> SEQ ID NO 51
<211> LENGTH: 5
<212> TYPE: PRT
<213> ORGANISM: Homo sapiens

<400> SEQUENCE: 51

Glu Lys Arg Cys Leu
1               5

<210> SEQ ID NO 52
<211> LENGTH: 5
<212> TYPE: PRT
```

```
<213> ORGANISM: Homo sapiens

<400> SEQUENCE: 52

Lys Arg Cys Leu Asn
1               5

<210> SEQ ID NO 53
<211> LENGTH: 5
<212> TYPE: PRT
<213> ORGANISM: Homo sapiens

<400> SEQUENCE: 53

Arg Cys Leu Asn Pro
1               5

<210> SEQ ID NO 54
<211> LENGTH: 5
<212> TYPE: PRT
<213> ORGANISM: Homo sapiens

<400> SEQUENCE: 54

Cys Leu Asn Pro Glu
1               5

<210> SEQ ID NO 55
<211> LENGTH: 5
<212> TYPE: PRT
<213> ORGANISM: Homo sapiens

<400> SEQUENCE: 55

Leu Asn Pro Glu Ser
1               5

<210> SEQ ID NO 56
<211> LENGTH: 11
<212> TYPE: PRT
<213> ORGANISM: Homo sapiens

<400> SEQUENCE: 56

Ala Thr Met Lys Lys Lys Gly Glu Lys Arg Cys
1               5                   10

<210> SEQ ID NO 57
<211> LENGTH: 17
<212> TYPE: PRT
<213> ORGANISM: Homo sapiens

<400> SEQUENCE: 57

Glu Ile Ile Ala Thr Met Lys Lys Lys Gly Glu Lys Arg Cys Leu Asn
1               5                   10                  15

Pro

<210> SEQ ID NO 58
<211> LENGTH: 14
<212> TYPE: PRT
<213> ORGANISM: Homo sapiens

<400> SEQUENCE: 58

Ala Thr Met Lys Lys Lys Gly Glu Lys Arg Cys Leu Asn Pro
1               5                   10

<210> SEQ ID NO 59
<211> LENGTH: 8
<212> TYPE: PRT
```

```
<213> ORGANISM: Artificial Sequence
<220> FEATURE:
<223> OTHER INFORMATION: Glycine spacer

<400> SEQUENCE: 59

Gly Gly Gly Gly Gly Gly Gly Gly
1               5

<210> SEQ ID NO 60
<211> LENGTH: 8
<212> TYPE: PRT
<213> ORGANISM: Artificial Sequence
<220> FEATURE:
<223> OTHER INFORMATION: Histidine spacer

<400> SEQUENCE: 60

His His His His His His His His
1               5

<210> SEQ ID NO 61
<211> LENGTH: 4
<212> TYPE: PRT
<213> ORGANISM: Homo sapiens

<400> SEQUENCE: 61

Lys Lys Gly Glu
1

<210> SEQ ID NO 62
<211> LENGTH: 4
<212> TYPE: PRT
<213> ORGANISM: Homo sapiens

<400> SEQUENCE: 62

Lys Arg Cys Leu
1

<210> SEQ ID NO 63
<211> LENGTH: 4
<212> TYPE: PRT
<213> ORGANISM: Homo sapiens

<400> SEQUENCE: 63

Lys Lys Lys Gly
1

<210> SEQ ID NO 64
<211> LENGTH: 4
<212> TYPE: PRT
<213> ORGANISM: Homo sapiens

<400> SEQUENCE: 64

Met Lys Lys Lys
1

<210> SEQ ID NO 65
<211> LENGTH: 6
<212> TYPE: PRT
<213> ORGANISM: Homo sapiens

<400> SEQUENCE: 65

Gly Glu Lys Arg Cys Leu
1               5

<210> SEQ ID NO 66
```

```
<211> LENGTH: 15
<212> TYPE: PRT
<213> ORGANISM: Artificial Sequence
<220> FEATURE:
<223> OTHER INFORMATION: Combined surface-binding peptides

<400> SEQUENCE: 66

Thr Met Lys Lys Lys Thr Met Lys Lys Lys Thr Met Lys Lys Lys
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Combined surface-binding peptide

<400> SEQUENCE: 67

Thr Met Lys Lys Lys Lys Lys Gly Glu Lys Arg Cys Leu Asn
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Combined surface-binding peptide

<400> SEQUENCE: 68

Thr Met Lys Lys Lys Thr Met Lys Lys Lys Lys Lys Gly Glu
1               5                   10                  15

<210> SEQ ID NO 69
<211> LENGTH: 6
<212> TYPE: PRT
<213> ORGANISM: Homo sapiens

<400> SEQUENCE: 69

Met Lys Lys Lys Gly Glu
1               5
```

SURFACE-BINDING PEPTIDE

SEQUENCE LISTING

The Sequence Listing submitted herewith, entitled "Nov-14-2017-Sequence-Listing ST25.txt", created Nov. 14, 2017, and having a size of 13,499 bytes, is incorporated herein by reference.

RELATED APPLICATION

The present application is a 371 of PCT/SE2014/051543 filed Dec. 19, 2014.

TECHNICAL FIELD

The present embodiments generally relate to surface-binding peptides, and in particular to the use of such surface-binding peptides for immobilizing molecules of interest on surfaces.

BACKGROUND

Implants and other medical devices implanted into the body of an animal or human body can trigger various immunological responses and rejection reactions. Such responses and reactions could prevent implantation of the medical device or affect the operation of the medical device in the body.

Accordingly, there is a general need for providing implants and medical devices with surfaces that prevent or at least reduce triggering immunological responses and rejection reactions in the host body. Various physical and chemical surface treating methods have been proposed in the art. The former includes coating the surface with various biocompatible materials, such as biocompatible metals or metal alloys, to present a biocompatible surface towards the immune system of the host body.

WO 2013/055749 discloses a chemical modification of implant surfaces to increase the immune tolerance of implantable medical devices. The surfaces of the implantable medical device are coated with one or more diketopiperazines.

However, so for there have been little progress in the art of biologically modifying surfaces of implants and medical devices using biomolecules such as proteins and enzymes. Hence, there is a need for a technology enabling modifying surfaces of such implants with various biomolecules.

SUMMARY

It is a general objective to provide a surface-binding peptide capable of binding to surfaces of various biocompatible materials.

It is a particular objective to provide a tool that can be used to tailor surfaces of implants and implantable medical device through immobilization of selected molecules of interest on the surfaces.

These and other objectives are met by embodiments as disclosed herein.

An aspect of the embodiments relates to an isolated surface-binding peptide consisting of N consecutive amino acids of an extended beta-hairpin motif EIIATMKKK-GEKRCLNP (SEQ ID NO: 57) in Interferon gamma-induced protein 10 (IP-10), wherein N=4-17, with the proviso that the isolated surface-binding peptide is not selected from the group consisting of KKGE (SEQ ID NO: 61), KRCL (SEQ ID NO: 62), KKKG (SEQ ID NO: 63), MKKK (SEQ ID NO: 64) and GEKRCL (SEQ ID NO: 65).

Another aspect of the embodiments relates to an isolated combined surface-binding peptide consisting of at least two surface-binding peptides according to above.

Yet another aspect of the embodiments relates to a surface-binding molecule comprising a surface-binding peptide linked to a heterologous molecule of interest. The surface-binding peptide is selected from the group consisting of a surface-binding peptide according to above, a surface-binding peptide comprising the amino acid sequence of ATMKK (SEQ ID NO: 20), a surface-binding peptide comprising the amino acid sequence of TMKKK (SEQ ID NO: 21), a surface-binding peptide comprising the amino acid sequence of MKKKG (SEQ ID NO: 22), a surface-binding peptide comprising the amino acid sequence of KKKGE (SEQ ID NO: 23), a surface-binding peptide comprising the amino acid sequence of KKGEK (SEQ ID NO: 48), a surface-binding peptide comprising the amino acid sequence of KGEKR (SEQ ID NO: 49), a surface-binding peptide comprising the amino acid sequence of GEKRC (SEQ ID NO: 50), a surface-binding peptide comprising the amino acid sequence of EKRCL (SEQ ID NO: 51), a surface-binding peptide comprising the amino acid sequence of KRCLN (SEQ ID NO: 52), and a surface-binding peptide comprising the amino acid sequence of RCLNP (SEQ ID NO: 53).

Further aspects of the embodiments relate to an artificial surface comprising a surface of a biocompatible material to which a surface-binding peptide according to above or a surface-binding molecule according to above is bound. In the latter case, the heterologous molecule of interest is attached to the surface through binding of the surface-binding peptide to the surface.

Additional aspects of the embodiments relate to a method of producing an artificial surface. The method comprises binding a surface-binding peptide according to above or a surface-binding molecule according to above to a surface of a biocompatible material. In the latter case, the heterologous molecule of interest is attached to the surface through binding of the surface-binding peptide to the surface.

Yet another aspect of the embodiments relates to a method of identifying a potentially biocompatible material. The method comprises contacting a material to be tested with a sample comprising a surface-binding peptide according to above and/or a surface-binding molecule according to above. The method also comprises detecting an amount of binding of the surface-binding peptide and/or the surface-binding molecule to a surface of the material to be tested. The method further comprises identifying the material to be tested as being potentially biocompatible based on the amount of binding of the surface-binding peptide and/or the surface-binding molecule to the surface.

A related aspect of the embodiments defines a kit for identifying a potentially biocompatible material. The kit comprises a surface-binding peptide according to above and/or a surface-binding molecule according to above. The kit also comprises instructions specifying that the surface-binding peptide and/or the surface-binding molecule should be contacted to a surface of a material to be tested in order to identify whether the material to be tested is potentially biocompatible based on an amount of binding of the surface-binding peptide and/or the surface-binding molecule to the surface.

BRIEF DESCRIPTION OF THE DRAWINGS

The embodiments, together with further objects and advantages thereof, may best be understood by making reference to the following description taken together with the accompanying drawings, in which:

FIG. 2 illustrates sequence alignment of IP-10 derived peptides and IP-10.

DETAILED DESCRIPTION

Figure 1:
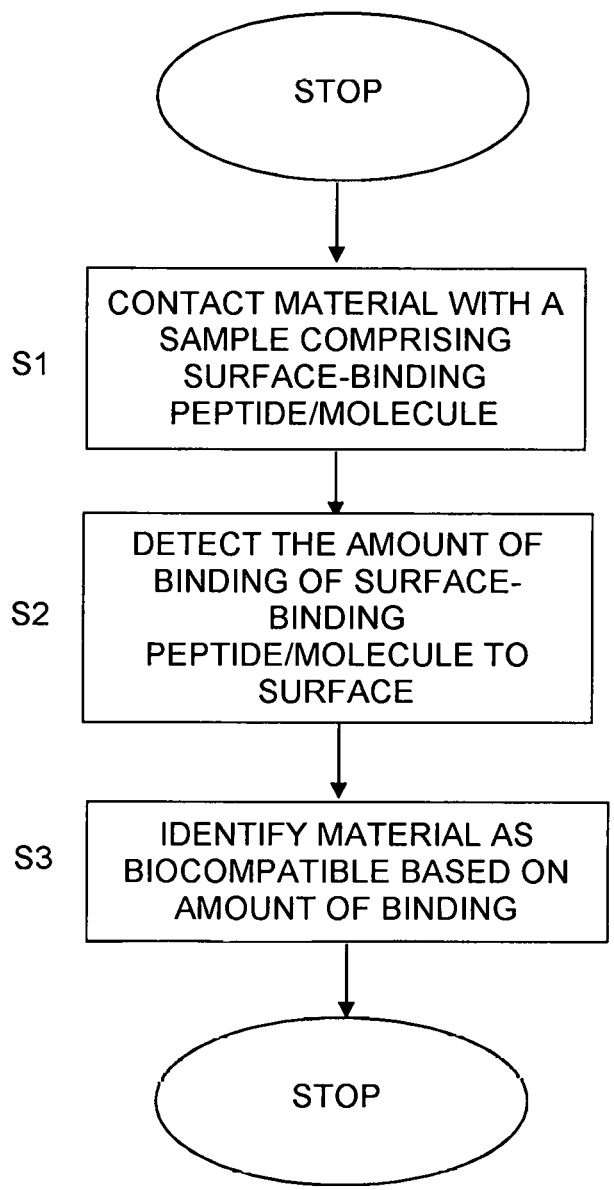
FIG. 1 is a flow diagram illustrating a method of identifying a potentially biocompatible material according to an embodiment.

The present embodiments generally relate to surface-binding peptides having the capability of binding to surfaces, such as surfaces of implants and implantable medical devices. Accordingly, the surface-binding peptides of the embodiments can be used as a tool or technology for attaching and immobilizing molecules of interest to such surfaces in order to impart or provide desired functions or characteristics to the surfaces through the attached molecules of interest.

The present embodiments thereby enable modifying and tailoring surfaces of, for instance, implants and implantable medical devices by providing a means to attach various molecules to the surfaces of the implants and implantable medical devices even if these molecules per se do not bind specifically or strongly to the surfaces. The surface-binding peptides of the embodiments can thereby, when directly or indirectly connected to the molecules, immobilize the molecules onto the surface by binding to the surface.

The surface-binding peptides of the embodiments are selected from a specific part of the protein Interferon gamma-induced protein 10 (IP-10), also referred to as C-X-C motif chemokine 10 (CXCL10) and small-inducible cytokine B10 in the art. IP-10 is a 8.7 kDa protein that in humans is encoded by the CXCL10 gene and belongs to the CXC chemokine family. IP-10 is secreted by various cell types, including monocytes, endothelial cells and fibroblasts, in humans in response to interferon-γ (IFN-γ). IP-10 has several roles including chemoattraction for monocytes, macrophages, T cells, NK cells and dendritic cells. The chemokine also promotes T cell adhesion to endothelial cells and has antitumor activity. IP-10 is further thought to inhibit bone marrow colony formation and angiogenesis. The chemokine exerts its effect by binding to the cell surface chemokine receptor CXCR3.

WO 2008/033069 discloses that metals selected from group 4 or 5 of the periodic table and oxides of such metals can be used to treat or prevent various diseases characterized by adverse IP-10 expression and/or release. The document discloses that these metals and metal oxides are capable of binding to IP-10 but also induce downregulation of production of IP-10.

The present embodiments are based on finding a particular portion of IP-10 that seems to be at least partly involved in the binding of IP-10 to various surfaces. Hence, the surface-binding peptides of the embodiments are derived from this particular portion of IP-10.

According to an aspect of the embodiments an isolated surface-binding peptide is provided. The isolated surface-binding peptide consists of N consecutive amino acids of an extended beta-hairpin motif in IP-10. This extended beta-hairpin motif corresponds to the following amino acid sequence EIIATMKKKGEKRCLNP (SEQ ID NO: 57). According to this aspect of the embodiments N=4-17, with the proviso that the isolated surface-binding peptide is not selected from the group consisting of KKGE (SEQ ID NO: 61), KRCL (SEQ ID NO: 62), KKKG (SEQ ID NO: 63), MKKK (SEQ ID NO: 64) and GEKRCL (SEQ ID NO: 65).

Hence, the isolated surface-binding peptide constitutes four to seventeen consecutive amino acids of the extended beta-hairpin motif EIIATMKKKGEKRCLNP (SEQ ID NO: 57) present in human IP-10. The expression extended beta-hairpin as used herein indicates that the amino acid sequence corresponds to the beta-hairpin motif EIIATMKKKGEKRC (SEQ ID NO: 19) and the three amino acids leucine (L), asparagine (N) and proline (P) directly following the beta-hairpin motif. Hence, the extended beta-hairpin as defined herein corresponds to the beta-hairpin motif and the three amino acids following the C-terminal of this beta-hairpin motif.

Figure 6:
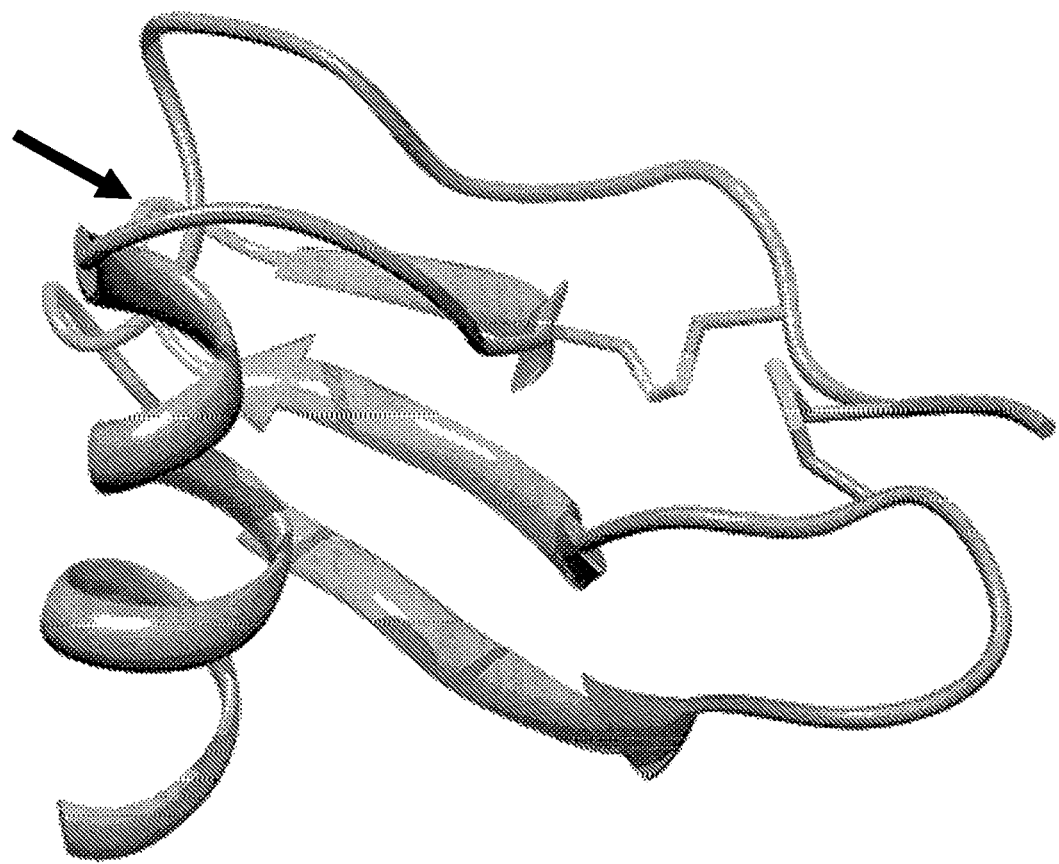
FIG. 6 is a three-dimensional illustration of the protein IP-10 indicating the beta-hairpin motif containing the sequence of the IP-10 derived short peptides.

FIG. 6 schematically illustrates a three-dimensional structure of human IP-10 with the beta-hairpin motif indicated by the arrow. It was very surprising that this particular portion of IP-10 is involved in binding to surfaces since there are other more exposed parts of IP-10 that would be more likely candidates for surface binding.

In an embodiment, the isolated surface-binding peptide preferably consists of N consecutive amino acids of the beta-hairpin motif EIIATMKKKGEKRC (SEQ ID NO: 19) in IP-10. In this embodiment, N is preferably 4 to 14, with the proviso that the isolated surface-binding peptide is not selected from the group consisting of KKGE (SEQ ID NO: 61), KKKG (SEQ ID NO: 63) and MKKK (SEQ ID NO: 64). Hence, in a particular embodiment the isolated surface-binding peptides are selected from the beta-hairpin motif and not the extended beta-hairpin motif.

Experimental data as presented herein shows that a selected portion of this beta-hairpin motif seems to be particularly involved in binding to surfaces. In more detail, it is the C-terminal portion of the beta-hairpin motif that has the strongest and best binding to surfaces. Hence, in an embodiment the isolated surface-binding peptide preferably consists of N consecutive amino acids of ATMKKKGEKRC (SEQ ID: NO: 56). In this embodiment, N is preferably 4 to 11, with the proviso that said isolated surface-binding peptide is not selected from the group consisting of KKGE (SEQ ID NO: 61), KKKG (SEQ ID NO: 63) and MKKK (SEQ ID NO: 64).

In addition to the C-terminal portion of the beta-hairpin motif also the portion in IP-10 directly following the C-terminal end of the beta-hairpin motif, i.e. the three amino acids L, N and P, seems to be particularly involved in surface binding as shown in the experimental data presented herein. Hence, in an embodiment the isolated surface-binding peptide preferably consists of N consecutive amino acids of ATMKKKGEKRCLNP (SEQ ID: NO: 58). In this embodiment, N is preferably 4 to 14, with the proviso that said isolated surface-binding peptide is not selected from the group consisting of KKGE (SEQ ID NO: 61), KRCL (SEQ ID NO: 62), KKKG (SEQ ID NO: 63), MKKK (SEQ ID NO: 64) and GEKRCL (SEQ ID NO: 65).

The isolated surface-binding peptide is preferably selected among quadromers, pentamers, hexamers, heptamers, octamers, nonamers and decamers, i.e. N is preferably 4 to 10, more preferably among quadromers, pentamers, hexamers and heptamers, i.e. N is preferably 4 to 7. In an embodiment, N is preferably 5, i.e. the isolated surface-binding peptide is preferably a pentamer.

In an embodiment relating to isolated surface-binding peptides in the form of pentamers, the isolated surface-binding peptide has an amino acid sequence selected from the group consisting of ATMKK (SEQ ID NO: 20), TMKKK (SEQ ID NO: 21), MKKKG (SEQ ID NO: 22), KKKGE (SEQ ID NO: 23), KKGEK (SEQ ID NO: 48), KGEKR (SEQ ID NO: 49), GEKRC (SEQ ID NO: 50), EKRCL (SEQ ID NO: 51), KRCLN (SEQ ID NO: 52), and RCLNP (SEQ ID NO: 53).

In another embodiment the isolated surface-binding peptide has an amino acid sequence selected from the group consisting of ATMKK (SEQ ID NO: 20), TMKKK (SEQ ID NO: 21), MKKKG (SEQ ID NO: 22), KKKGE (SEQ ID NO: 23), KRCLN (SEQ ID NO: 52), and RCLNP (SEQ ID NO: 53).

Another aspect of the embodiments relates to an isolated combined surface-binding peptide. Such an isolated combined surface-binding peptide consists of multiple, i.e. at least two, surface-binding peptides as defined in the foregoing. Hence, a combined surface-binding peptide is basically a combination of at least two different surface-binding peptides and/or a combination of at least two copies of a same surface-binding peptide. Thus, a general formula of such an isolated combined surface-binding peptide is $[Bq]_p$, wherein $p \geq 2$ and $q=0, \ldots, p-1$ and Bq denotes the amino acid sequence of a surface-binding peptide according to the embodiments and as defined above. Note that all Bq of the isolated combined surface-binding peptide could have the same amino acid sequence, all Bq could have different amino acid sequences or some of the Bq of the combined surface-binding peptide could have the same amino acid sequence and the other of the p Bq could have different amino acid sequences. An example of the former is TMKKK-TMKKK-TMKKK (SEQ ID NO: 66), whereas examples of the latter two cases could be TMKKK-KK-GE-KRCLN (SEQ ID NO: 67) and TMKKK-TMKKK-KKKGE (SEQ ID NO: 68), respectively.

In an embodiment, the isolated combined surface-binding peptide preferably consists of at least two surface-binding peptides in the form of quadromers, pentamers or hexamers, preferably in the form of pentamers. In such an embodiment, the isolated combined surface-binding peptide preferably consists of at least two but no more than eight, preferably at least two but no more than six and more preferably at least two but no more than four such surface-binding peptides. Hence, in these embodiments p=2-8, preferably p=2-6 and more preferably p=2-4.

The surface-binding peptides of the isolated combined surface-binding peptide are preferably selected from the group consisting of ATMKK (SEQ ID NO: 20), TMKKK (SEQ ID NO: 21), MKKKG (SEQ ID NO: 22), KKKGE (SEQ ID NO: 23), KKGEK (SEQ ID NO: 48), KGEKR (SEQ ID NO: 49), GEKRC (SEQ ID NO: 50), EKRCL (SEQ ID NO: 51), KRCLN (SEQ ID NO: 52), and RCLNP (SEQ ID NO: 53).

In another embodiment the surface-binding peptide are preferably selected from the group consisting of ATMKK (SEQ ID NO: 20), TMKKK (SEQ ID NO: 21), MKKKG (SEQ ID NO: 22), KKKGE (SEQ ID NO: 23), KRCLN (SEQ ID NO: 52), and RCLNP (SEQ ID NO: 53).

As was mentioned in the foregoing the surface-binding peptides of the embodiments, i.e. the isolated surface-binding peptides and/or the isolated combined surface-binding peptides, can be used to attach or immobilize molecules of interest onto a surface. Hence, embodiments also relate to a surface-binding peptide linked or connected to a heterologous molecule of interest. Linked as used herein encompasses that the surface-binding peptide can be directly connected and bound to the heterologous molecule of interest. Linked as used herein also encompasses that the surface-binding peptide can be indirectly connected or bound to the heterologous molecule of interest using a linker or spacer.

Heterologous molecule of interest indicates that the molecule of interest is directly or indirectly connected to the surface-binding peptide to form a new, artificial molecule, denoted surface-binding molecule herein, comprising the molecule of the interest, the surface-binding peptide and optionally any linker or spacer.

Accordingly, a further aspect of the embodiments relates to a surface-binding molecule comprising a surface-binding peptide linked to a heterologous molecule of interest. The surface-binding peptide of the surface-binding molecule is selected from the group consisting of a surface-binding peptide as defined in the foregoing, a surface-binding peptide comprising the amino acid sequence of ATMKK (SEQ ID NO: 20), a surface-binding peptide comprising the amino acid sequence of TMKKK (SEQ ID NO: 21), a surface-binding peptide comprising the amino acid sequence of MKKKG (SEQ ID NO: 22), a surface-binding peptide comprising the amino acid sequence of KKKGE (SEQ ID NO: 23), a surface-binding peptide comprising the amino acid sequence of KKGEK (SEQ ID NO: 48), a surface-binding peptide comprising the amino acid sequence of KGEKR (SEQ ID NO: 49), a surface-binding peptide comprising the amino acid sequence of GEKRC (SEQ ID NO: 50), a surface-binding peptide comprising the amino acid sequence of EKRCL (SEQ ID NO: 51), a surface-binding peptide comprising the amino acid sequence of KRCLN (SEQ ID NO: 52), and a surface-binding peptide comprising the amino acid sequence of RCLNP (SEQ ID NO: 53).

In an embodiment of the surface-binding molecule, the surface-binding peptide is preferably selected from the group consisting of a surface-binding peptide comprising the amino acid sequence of ATMKK (SEQ ID NO: 20), a surface-binding peptide comprising the amino acid sequence of TMKKK (SEQ ID NO: 21), a surface-binding peptide comprising the amino acid sequence of MKKKG (SEQ ID NO: 22), a surface-binding peptide comprising the amino acid sequence of KKKGE (SEQ ID NO: 23), a surface-binding peptide comprising the amino acid sequence of KRCLN (SEQ ID NO: 52), and a surface-binding peptide comprising the amino acid sequence of RCLNP (SEQ ID NO: 53).

In the above-described embodiments the surface-binding peptide of the surface-binding molecule comprises one of the listed amino acid sequences. This means that the surface-binding peptide may additionally comprise at least one other amino acid in addition to the five specifically stated amino acid residues.

In another embodiment, the surface-binding peptide of the surface-binding molecule is selected from the group consisting of a surface-binding peptide having the amino acid sequence of ATMKK (SEQ ID NO: 20), a surface-binding peptide having the amino acid sequence of TMKKK (SEQ ID NO: 21), a surface-binding peptide having the amino acid sequence of MKKKG (SEQ ID NO: 22), a surface-binding peptide having the amino acid sequence of KKKGE (SEQ ID NO: 23), a surface-binding peptide having the amino acid sequence of KRCLN (SEQ ID NO: 52), and a surface-binding peptide having the amino acid sequence of RCLNP (SEQ ID NO: 53).

In an embodiment, the surface-binding peptide of the surface-binding molecule is directly connected or bound to the heterologous molecule of interest. In such a case, any known technique for connecting an amino acid to another molecule, such as an organic molecule or a protein, polypeptide or antibody, can be used. Non-limiting examples include techniques for attaching the heterologous molecule of interest to the amine group at the N-terminal or the carboxyl group at the C-terminal, such as using aminohexanoic acid.

In another embodiment, the surface-binding peptide is linked to the heterologous molecule of interest through a spacer or linker. In this embodiment, any known technique of using linkers or spacers to interconnect an amino acid sequence with a molecule, such as an organic molecule or a protein, polypeptide or antibody, can be used.

A non-limiting example is to use a spacer denoted as $X_n$, wherein X denotes an amino acid and n is 3 to 20. In an embodiment, X preferably represents a glycine residue. In another embodiment, X preferably represents a histidine residue. In an embodiment, n is preferably 4 to 12 and more preferably n=8. Hence, a particular example of a spacer that could be used according to the embodiments is an octamer of glycine residues, i.e. GGGGGGGG (SEQ ID NO: 59), or an octamer of histidine residues, i.e. HHHHHHHH (SEQ ID NO: 60).

Also spacers, links or linkers other than amino acid spaces could be used according to the embodiments. For instance, a link in the form of a straight or branched $C_m$ chain could be used. In an embodiment m is preferably 3 to 20 and more preferably 4 to 12. In a particular embodiment, the link is a straight or branched alkyl chain, such as straight or branched $C_{4-12}$ alkyl chain. Non-limiting examples include a butyl chain, a pentyl chain, a hexyl chain, a heptyl chain, an octyl chain, a nonyl chain, a decyl chain, an undecyl chain and a dodecyl chain. Also $C_m$ chains containing one or multiple double and/or triple, —HC=CH— and/or —C≡C—, bonds are possible for use as links according to the embodiments.

Further examples of spacers or links that can be used according to the embodiments include a streptavidin and biotin link and an avidin and biotin link.

The heterologous molecule of interest linked to the surface-binding peptide to form the surface-binding molecule could be any molecule or biomolecule that should be attached, using the surface-binding peptide, to a surface as disclosed herein. The embodiments thereby enable basically any type of molecule that can be linked to the surface-binding peptide to be immobilized onto a surface through its direct or indirect connection to the surface-binding peptide and the binding of the surface-binding peptide to the surface.

The below provided list of heterologous molecules should merely be seen as an illustrative and non-limiting list of molecules that could be used in the surface-binding molecule of the embodiments. The embodiments are, however, not limited thereto and encompasses any heterologous molecule that can be linked directly or indirectly to a surface-binding peptide of the embodiments.

The heterologous molecule of interest could be selected among markers, such as fluorescent markers, i.e. a fluorophore, e.g. fluorescein isothiocyanate (FITC), tetramethyl-rhodamine isothiocyanate (TRITC) and other isothiocyanates; N-hydroxysuccinimide (NHS) fluorescein and other succinimidyl esters; fluorescein-5-maleimide and other maleimide activated fluorophores; cyanine fluorophores; fluroescein fluorophores; rhodamine fluorophores; ATTO dyes; DyLight Fluor dyes; Alexa Fluor dyes; and borondipyrromethene (BODIPY) dyes. Further examples include isotope labels or markers, chemiluminescent markers, radiopaque markers, etc. In such a case, the surface-binding molecule can be used as a test molecule to enable detection, using the marker, of the surface-binding molecule on a surface. Such a type of surface-binding molecule can advantageously be used to test binding of the surface-binding molecule to various test surfaces in a method of identifying a potentially biocompatible materials as further described herein.

Further examples of heterologous molecules include cell adhesion and cell attachment molecules, such cell adhesion molecules (CAMs), including immunoglobulin (Ig) superfamily, integrins, cadherins and selectins. In such a case, the surface-binding molecule can be used to attach cells onto a surface by the interaction between the cell adhesion molecule of the surface-binding molecule and the cells.

A further example of a heterologous molecule is extracellular matrix (ECM) molecules including, for instance, proteoglycans (PGs), glycosaminoglycans (GAGs), heparan sulfate (HS), chondroitin sulfates, keratin sulfates, collagen, elastins, etc. The surface-binding molecule can then be used to bind cells onto a surface, similar to using cell adhesion molecules as heterologous molecule of interest.

A related type of molecular of interest is basal lamina molecules that include molecules of the basal lamina, which is a layer of ECM secreted by epithelial cells. Non-limiting examples of such basal lamina molecules include laminin, type IV collagen, entactin and perlecan. Also in this example, the surface-binding molecule can be used to bind cells onto a surface.

Yet another example of a heterologus molecule of interest is an anti-inflammatory molecule, such as corticosteroids; glucocorticoids; non-steroidal anti-inflammatory drugs (NSAIDs), such as acetylsalicylic acid, iso-butyl-propanoic-phenolic acid and naproxen sodium (INN); lipoxins; interleukin-1 receptor antagonist (IL-1RA); etc. The surface-binding molecule can then be used to reduce or inhibit local inflammation in a body of a human or animal into which an implant or other implantable medical device is implanted. The surfaces or at least a portion thereof of the implant or implantable medical device can then be coated by surface-binding molecules comprising anti-inflammatory molecules that are attached to the surface through the surface-binding peptides. Accordingly, the local inflammatory reaction that otherwise occurs when a foreign material is implanted into the body can be suppressed or at least reduced by using this type of surface-binding molecule.

Antibiotics can also be used as heterologus molecules of interest in order to inhibit bacterial growth or kill bacteria. Non-limiting examples of antibiotics include penicillins; cephalosporins; polymyxins; rifamycins; lipiarmycins; quinolones; sulfonamides; macrolides; lincosamides; tetracylines; bactericidal aminoglycosides; cyclic lipopeptides, such as daptomycin; glycylcylines, such as tigecycline; oxazolidones, such as linezolid; and lipiarmycins, such as fidaxomicin. Such a heterologous molecule of interest provides a surface-binding molecule with bacteriostatic or bactericidal activity. Accordingly, an implant or other implantable medical device with a surface coated with such surface-binding molecules will provide a local antibacterial effect, thereby significantly reducing the risk of local bacteria infection, for instance, in connection with implantation of the implant or implantable medical device.

In a similar way molecules targeting other types of microbes, such as anti-fungal molecules, e.g. polyene antifungals, such as amphotericin B, candicidin, filipin, hamycin, natamycin, nystatin and rimocidin; azole anti-fungals, such as imidazoles, e.g. bifonazole, butoconazole, clotrimazole, econazole, fenticonazole, isoconazole, miconazole, omoconazole, oxiconazole, sertaconazole, sulconazole and tioconazole; triazoles, e.g. albaconazole, fluconazole, isavuconazole, itraconazole, posaconazole, ravuconazole, terconazole and voriconazole; and thiazoles, e.g. abafungin; allylamines, such as amorolfin, butenafine, naftifine and terbinafine; echinocandins, such as anidulafungin, caspofungin and micafungin; benzoic acid; ciclopirox olamine; flucytosine; griseofulvin; tolnaftate and undecylenic acid. Also anti-viral molecules, e.g. virus-assisted protein (VAP) anti-idiotypic antibodies; amantadine; rimantadine; pleconaril; acyclovir; zidovudine (AZT); lamivudine; integrase; fomivirsen; rifampicin; zanamivir and oseltamivir, and anti-parasitic molecules, such as mebendazole; pyrantel pamoate; thiabendazole; diethylcarbamazine; ivermectin; niclosamide; praziquantel; albendazole; praziquantel; rifampin; amphotericin B; melarosprol; elfornithine; metronidazole; tinidazole and miltefosine, could be used as heterologous molecule of interest. Thus, generally any anti-microbial molecule could be used to in the surface-binding molecule to provide an anti-microbial effect onto a surface to which the surface-binding molecule is attached.

A further example of heretologous molecules include growth factors, such as adenomedullin (AM), angiopoietin (Ang), autocrine motility factor, bone morphogenetic proteins (BMPs), brain-derived neutrophic factor (BDNF), epidermal growth factor (EGF), erythropoietin (EPO), fibroblast growth factor (FGF), glial cell line-derived neutrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), mystatin (GDF-8), nerve growth factor (NGF), platelet-derived growth factor (PDGF), thrombopoietin (TPO), transforming growth factor alpha (TGF-α), transforming growth factor beta (TGF-β), tumor necrosis factor alpha (TNF-α), vascular endothelial growth factor (VEGF), placental growth factor (PlGF), etc. A surface-binding molecule comprising a growth factor linked to a surface-binding peptide can be used to provide a surface with, for instance, capability of stimulating cellular growth, proliferation and/or cellular differentiation.

Further examples of heterologus molecules of interest include cell growth inhibitors and chemotherapeutic agents. Such a type of heterologous molecules will, when included in the surface-binding molecule, provide a local cell growth inhibiting effect around a surface to which the surface-binding molecule is attached. Non-limiting examples of such heretologus molecules of interest include farnesyl transferase inhibitors; alkylating agents, such as nitrogen mustards, e.g. mechlorethamine, cyclophosphamide, melphalan, chlorambucil, ifosfamide and busulfan; nitrosoureas, e.g. N-nitroso-N-methylurea (MNU), carmustine (BCNU), lomustine (CCNU), semustine (MeCCNU), fotemustine and streptozotocin; tetrazines, e.g. dacarbazine, mitozolomide and temozolomide and aziridines, e.g. thiotepa, mytomycin, diaziquone (AZQ); and cisplatines, e.g. cisplatine, carboplatin and oxaplatin; anti-metabolites, such as anti-folates, e.g. methotrexate and pemetrexed; fluropyrimidines, e.g. fluorouracil and capecitabine; deocynucleoside analogues, such as cytarabine, gemcitabine, decitabine, Vidaza, fludarabine, nelarabine, cladribine, clofarabine and pentostatine; and thiopurines, e.g. thiguanine and mercaptopurine; anti-microtubule agents, such as vinca alkaloids, e.g. vincristine, vinblastine, vinorelbine, vindesine and vinflunine; and taxanes, e.g. paclitaxel and docetaxel; and podophyllotxin; topoisomerase inhibitors, such as irinotecan, topotecan, captothecin, etoposide, doxorubicin, mitoxantrone, teniposide, novobiocine, merbarone and aclarubicin; cytotoxic antibiotics, such as antracyclines, e.g. doxorubicin, daumorubicin, epirubicin, idarubicin, pirarubicin, aclarubicin, mitoxantrone, actinomycin, bleomycin, plicamycin, and mitomycin.

The surface-binding molecule of the embodiments can comprise various enzymes that become immobilized onto a surface using the surface-binding molecules. Any type of enzyme that can be linked to the surface-binding peptides can be used in order to provide local enzymatic reactions and functions at a surface.

Other groups of heterologous molecules of interest include antibodies, DNA molecules, RNA molecules, receptors, ligands and antibodies.

A further aspect of the embodiments relates to an artificial surface comprising a surface of a biocompatible material to which a surface-binding peptide according to the embodiments is attached. Another aspect of the embodiments relates to an artificial surface comprising a surface of a biocompatible material to which a surface-binding molecule of the embodiments is bound. In this aspect the heterologous molecule of interest in the surface-binding molecule is attached to the surface through binding of the surface-binding peptide of the surface-binding molecule to the surface.

Figure 13:
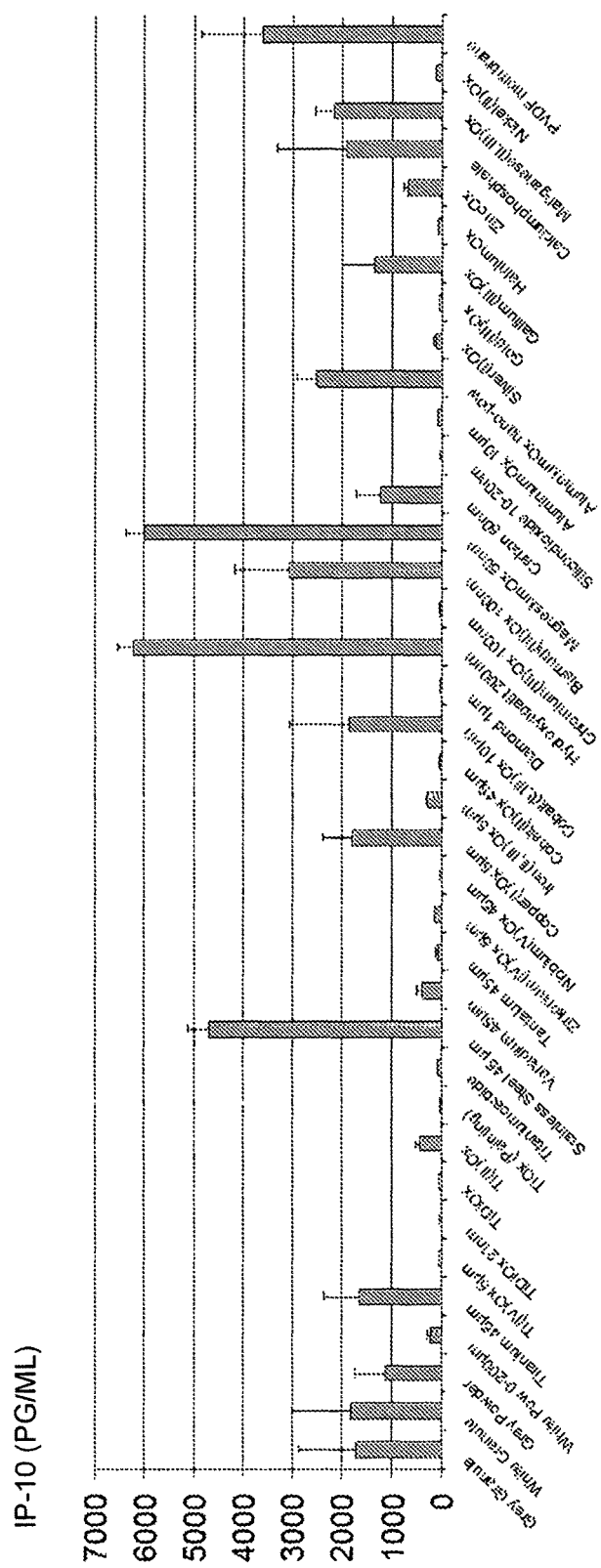
FIG. 13 is a diagram illustrating an amount of IP-10 left in solution after incubation of 20 mg of respective material in 12 ng/ml solution. Values represent the mean±SEM (n=4).

As is further disclosed herein, the surface-binding peptides of the embodiments bind particularly to surfaces of biocompatible materials, see FIG. 13. Biocompatible as used herein generally denotes that the material is not toxic and does not cause any long term injurious effect on a body of a human or animal when introduced in the body. Biocompatibility of an implant and implantable medical device generally implies the capability of the implant or implantable medical device implanted in the body to exist in harmony with the tissue without causing deleterious changes.

In a particular embodiment, the biocompatible material is preferably selected from a metal of group 4 or 5 of the periodic table of the elements, an oxide of a metal of group 4 or 5 of the periodic table of the elements, silver, an oxide of silver, gold, and an oxide of gold, and an oxide of silicon. The oxide of silver is preferably silver(I) oxide, i.e. $Ag_2O$, the oxide of gold is preferably gold(III) oxide, $Au_2O_3$, and the oxide of silicon is preferably silicon dioxide, i.e. $SiO_2$, also known as silica.

The biocompatible material is more preferably a metal of group 4 or 5 of the periodic table of the elements selected among titanium, zirconium, hafnium, niobium and tantalum and the oxide of a metal of group 4 or 5 of the periodic table of the elements is preferably selected among an oxide of titanium, an oxide of zirconium, an oxide of hafnium, an oxide of niobium and an oxide of tantalum.

Titanium has three oxidation state, Ti(II), Ti(III) and Ti(IV). The present embodiments can use any of these oxides of titanium, i.e. Ti(II) oxide, Ti(III) oxide and Ti(IV) oxide. Ti(IV) oxide is also denoted titanium dioxide ($TiO_2$) or titania in the art. This titanium dioxide is a preferred oxide form of titanium according to the present embodiments. $TiO_2$ can be present in different mineral or crystalline forms, including rutile, anatase and brookite. Rutile is a tetragonal mineral usually of prismatic habit, anatase or octahedrite is a tetragonal mineral of dipyramidal habit, while brookite is an orthorhombic mineral. A preferred titanium dioxide according to the present embodiments is preferably in the rutile form or a mixture of the rutile and the anatase form.

A preferred oxide of zirconium is Zr(IV) oxide and Hf(IV) oxide is a preferred hafnium oxide. Niobium oxide can be in the form of Ni(V) oxide or Ni(III) oxide and tantalum has oxidation states of Ta(II), Ta(IV) and Ta(V).

A particularly preferred biocompatible material of the present embodiments is titanium and an oxide of titanium, preferably $TiO_2$. As is well known in the art, a titanium material exposed to air will become oxidized forming a thin titanium dioxide layer on the titanium material. Hence, a titanium product as used herein most likely has a titanium dioxide surface exposed to the exterior of the titanium product.

Surface-binding peptide as defined herein relates, in an embodiment, to a peptide capable of binding to a surface as described herein, and in particular binding to a surface of a metal of group 4 or 5 of the periodic table of the elements selected among titanium, zirconium, hafnium, niobium and tantalum and/or an oxide thereof, i.e. an oxide of titanium, an oxide of zirconium, an oxide of hafnium, an oxide of niobium and/or an oxide of tantalum.

The surface, to which the surface-binding peptide of the embodiments binds, is preferably a surface of an implant or an implantable medical device. Non-limiting but illustrative examples of such implants and implantable medical devices include stents, artificial heart valves, pacemakers, implantable cardioverter-defibrillators, medical leads and catheters, implantable pumps, such as implantable insulin pumps, prostheses, implantable screws, etc.

The surface-binding peptides of the embodiments can thereby be used to tailor the surfaces or part thereof of such implants and implantable medical devices to get a local target effect around and close to the surfaces of the implants and implantable medical devices.

Also other types of implants could be coated with surface-binding peptides and molecules of the embodiments including grains, granules or particles, such as microparticles or nanoparticles, for instance, titanium micro- or nanoparticles, of biocompatible materials. Such grains, granules or particles have been used, for instance, in connection with anchoring and stabilizing prostheses, such as hip prostheses, and treatment of injured verterbra, for instance by injecting such grains, granules or particles by vertebroplasty or kyphoplasty to treat vertebral compression fractures.

In particular, nanoparticles have been suggested as carrier for various medicaments and active substances. For instance, nanoparticles as carrier for cytostatics have been used for cancer treatment. Nanoparticles, such as titanium nanoparticles, could then be used together with surface-binding peptides of the present embodiments in order to immobilize various medicaments and active substances to the nanoparticles. The surface-binding peptides can also be used to immobilize homing molecules that will direct the nanoparticles to target cells in the patient body. These homing molecules can be any molecule that binds to the target cells including, for instance, antibodies, ligands and receptors.

For instance, nanoparticles having cytostatics and cancer homing molecules immobilized to the nanoparticles by the surface-binding peptides of the embodiments could be used in systemic administration but achieve local anti-cancer cells. Thus, the immobilized homing molecules direct the administered nanoparticles to the cancer cells in the patient body, where the immobilized cytostatics will provide a local cytotoxic effect to the cancer cells.

Thus, the surface-binding peptides of the embodiments can advantageously be used to immobilize various types of heterologous molecules to nanoparticles, including homing molecules and medicaments.

The surface-binding peptides can also be used to bind various types of cells to surfaces, such as surfaces of implants or implantable medical devices. The surface-binding molecules of the embodiments then preferably comprises a molecule, such as ligand or receptor, to which the target cells will bind. A non-limiting example of cell type is stem cells.

In a particular embodiment, the surface of the implant or implantable medical device that should be coated with surface-binding molecules or peptides of the embodiments is preferably contacted with the surface-binding molecules or peptides, such as a solution comprising the surface-binding molecules or peptides, prior to implantation. Surface-binding molecules or peptides present in the solution will then bind to the immersed surface to thereby attach the heterologous molecule of interest in the surface-binding molecule onto the surface through the binding of the surface-binding peptide to the surface.

In another or complementary embodiment, the implant or implantable medical device is first implanted into the body of the animal or human host. The surface-binding molecules or peptides are then administered to the body, such as in the form of an injection solution comprising the surface-binding molecules or peptides. The administration is preferably in the form of a local administration at the site of implantation of the implant or implantable medical device but could alternatively be a systemic administration if the surface-binding molecule or peptide is able to be transferred from the administration site to the implantation site. Once the surface-binding molecules or peptides reach the surface of the implant or implantable medical device they will bind to the surface.

As a consequence, the surface-binding molecule of the embodiments could be used as a delivery vehicle to direct a heterologous molecule of interest onto a surface of an implant or implantable medical device and anchor the heterologous molecule of interest to the surface.

The artificial surface of the implant or implantable medical device could be coated with various types of heterologous molecules of interest, for instance, selected from the previously mentioned groups of heterologous molecules of interest. In such a case, a first group or set of surface-binding molecules could comprise a first heterologous molecule of interest, whereas at least one second group or set of surface-binding molecules could instead comprise at least one second, different heterologous molecule of interest. The at least two groups or sets of surface-binding molecules may comprise the same or different surface-binding peptides of the embodiments. Hence, it is, with this approach, possible to get a cocktail of different heterologous molecules of interest attached to a same surface or to different surface portions of an implant or implantable medical device.

An aspect of the embodiments relates to a method of producing an artificial surface. The method comprises binding a surface-binding peptide according to the embodiments to a surface of a biocompatible material. In another embodiment, the method comprises binding a surface-binding molecule of the embodiments to a surface of a biocompatible material. The heterologous molecule of interest of the surface-binding molecule then becomes attached to the surface through binding of the surface-binding peptide of the surface-binding molecule to the surface.

The binding step of these methods preferably comprises contacting the surface with the surface-binding molecule or peptide, such as contacting the surface of the biocompatible material with a solution comprising the surface-binding molecule or peptide. For instance, the surface can be immersed into the solution comprising the surface-binding molecule or peptide.

The solution is preferably an aqueous solution, such as a saline solution or a buffered solution, such as a phosphate buffered saline (PBS) solution.

Experimental data as presented herein indicates that the chemokine IP-10 binds specifically to materials that are generally regarded as being biocompatible, see FIG. 13. Accordingly, the surface-binding molecule or peptide of the embodiments also bind in particular to biocompatible materials and less to materials that are toxic to the human or animal body. The surface-binding molecules and peptides of the embodiments can thereby be used to identify whether a material is potentially biocompatible or not. Hence, the embodiments can be used as an initial screening test to see whether a material could be potentially biocompatible as assessed whether the surface-binding molecules or peptides bind at sufficiently high amount to a surface of the material to be tested.

The screening test as disclosed herein does not provide an absolute verification whether a material is biocompatible or not but can be used as an easy test to discriminate whether a material should be further tested for biocompatibility using other tests (binds a sufficient amount of the surface-binding molecule or peptide) or not be further tested for biocompatibility (does not bind a sufficient amount of the surface-binding molecule or peptide). Hence, the method and kit of the embodiments can be used to provide decision support whether to perform further biocompatibility tests of a material or not.

An aspect of the embodiments relates to a method of identifying a potentially biocompatible material. FIG. 1 is a flow diagram illustrating an embodiment of such a method. The method comprises contacting, in step S1, a material to be tested with a sample comprising a surface-binding peptide and/or a surface-binding molecule of the embodiments. A next step S2 comprises detecting an amount of binding of the surface-binding peptide and/or the surface-binding molecule to a surface of the material to be tested. The material to be tested is then identified in step S3 as being potentially biocompatible based on the amount of binding of the surface-binding peptide and/or the surface-binding molecule to the surface.

The sample that is used in step S1 is preferably a solution comprising the surface-binding peptide and/or the surface-binding molecule as previously described herein. The material can thereby be fully or at least partly immersed in the solution in step S1.

Step S3 preferably comprises identifying the material as being potentially biocompatible based on a comparison of the amount of binding as detected in step S2 with a defined threshold value. Hence, if the detected amount of binding is equal to or exceeds the threshold value the material is identified as being potentially biocompatible. However, if the detected amount of binding is below the threshold value the material is not regarded as being biocompatible. The threshold value could be expressed as the molar strength or the amount of bound surface-binding peptide and/or surface-binding molecule per surface unit, such as $mol/m^2$. A further variant of threshold value is to indicate a percentage of coverage of the surface with the surface-binding peptide or molecule. In such a case, the threshold value could define the minimum percentage of coverage to be achieved for a defined surface area.

In a particular embodiment, the contacting step S1 preferably comprises contacting the material to be tested with a sample comprising a surface-binding molecule according to the embodiments. In this embodiment, the heterologous molecule of interest is a marker that is easily detectable. In such a case, the detecting step S2 preferably comprises detecting the amount of binding of the surface-binding molecule to the surface by measuring the amount of the marker attached to the surface through the surface-binding peptides of the embodiments.

The marker is advantageously a fluorescent molecule. In such a case, the detection in step S2 could be performed by fluorescence measurements. Alternatives include using heterologous molecules of interest that comprise radionucleotides, in which case step S2 involves radioactivity measurements. Also enzymes could be used for detection purposes. For instance, the heterologous molecule of interest could be a streptavidin/avidin or a biotin molecule. In such a case, an enzyme-bound biotin or streptavidin/avidin, such as horseradish peroxidise (HRP), is added to bind to the surface-binding molecule. Alternatively, the heterologous molecule could be the enzyme, such as HRP, using a strepatividn/avidin and biotin link to attach the enzyme to the surface-binding peptide. A substrate of the enzyme is added to form a product that is easily detectable, such as using spectrophotometric methods. Other techniques of detection in step S2 could be based on antibodies, such as labelled antibodies, that specifically bind to the heterologous molecule of interest. Alternatively, the heterologous molecule of interest could be an antibody to which an antigen, such as labelled antigen, is added for detection purposes. Also visual inspection of the surface could be possible using, for instance, microscopes. In such a case, the heterologous molecule of interest could be a gold, silver or plastic bead, such as nano bead. Also ferromagnetic beads could be used as heterologous molecule of interest.

A related aspect of the embodiments defines a kit for identifying a potentially biocompatible material The kit comprises a surface-binding peptide and/or a surface-binding molecule according to the embodiments. The kit preferably also comprises instructions specifying that the surface-binding peptide and/or surface-binding molecule should be contacted to a surface of a material to be tested in order to identify whether the material to be tested is potentially biocompatible based on the amount of binding of the surface-binding peptide and/or surface-binding molecule to the surface.

The kit preferably also comprises information of the previously described threshold value.

EXPERIMENTS

Experiment 1: Localization of Surface-Binding Region in IP-10

This experiment was conducted to find the exact region of the IP-10 molecule that binds to titanium. In this experiment the effect of $TiO_2$ (diameter ~14 nm, product number P 90, Aerosil Evonic Ind.) on peptides synthesized from the IP-10 molecule by absorbance measurements using a Spektro U29-10 Hitachi spectrophotometer.

Materials and Methods

Seventeen different peptides having sequences of various portion of IP-10 were dissolved in water and thereafter diluted to working solution (50 µg/mL) in phosphate buffered saline (PBS), see Table 1 and FIG. 2.

TABLE 1

IP-10 derived peptides for localizing binding site

| Identification of peptide | Amino acid sequence | SEQ ID NO: |
|---|---|---|
| Peptide 1 | VPLSRTVRCTCISISNQPVN | 1 |
| Peptide 2 | CISISNQPVNPRSLEKLEII | 2 |
| Peptide 3 | PRSLEKLEIIPASQFCPRVE | 3 |
| Peptide 4 | PASQFCPRVEIIATMKKKGE | 4 |
| Peptide 5 | IIATMKKKGEKRCLNPESKA | 5 |
| Peptide 6 | IKNLLKAVSKERSKRSP | 6 |
| Peptide 7 | KAIKNLLKA | 7 |
| Peptide 8 | CTCISISNQPVNPRSLEKLEIIPASQFC | 8 |

TABLE 1-continued

IP-10 derived peptides for localizing binding site

| Identification of peptide | Amino acid sequence | SEQ ID NO: |
|---|---|---|
| Peptide 9 | FCPRVEPASQ | 9 |
| Peptide 10 | EPASQFCPRV | 10 |
| Peptide 11 | FCPRVEIIAT | 11 |
| Peptide 12 | MKKKGEIIAT | 12 |
| Peptide 13 | EIIATMKKKG | 13 |
| Peptide 14 | PASQFCPRVE | 14 |
| Peptide 15 | EIIATMKKKGE | 15 |
| Peptide 16 | CPRVEIIATM | 16 |
| Peptide 17 | SQFCPRVEIIATMKKK | 17 |

Peptides 1-6 collectively span the whole sequence of IP-10 as shown in FIG. 2. Peptides 7-17 cover various specific portions of IP-10. Please note that peptides 9, 10, 12 each contains an N-terminal or C-terminal portion of the IP-10 sequence moved to the C-terminal or N-terminal portion of the peptide, see underlined amino acids in FIG. 2.

The absorbance of the peptides bound to $TiO_2$ surfaces P90 from Sigma-Aldrich) were measured at 206 nm using a Spektro U29-10 Hitachi spectrophotometer. Briefly, 20 mg $TiO_2$ (P90) was incubated with 250 µl of peptide solution. After 3 h incubation on a shaking device in room temperature, with vortexing every hour, the samples were centrifuged (13 000×g, 3 min) and the supernatant was collected. As a negative control, PBS alone was used and positive control was peptide solution alone. Every sample was made in double and the experiments were repeated.

Results

Figure 3:
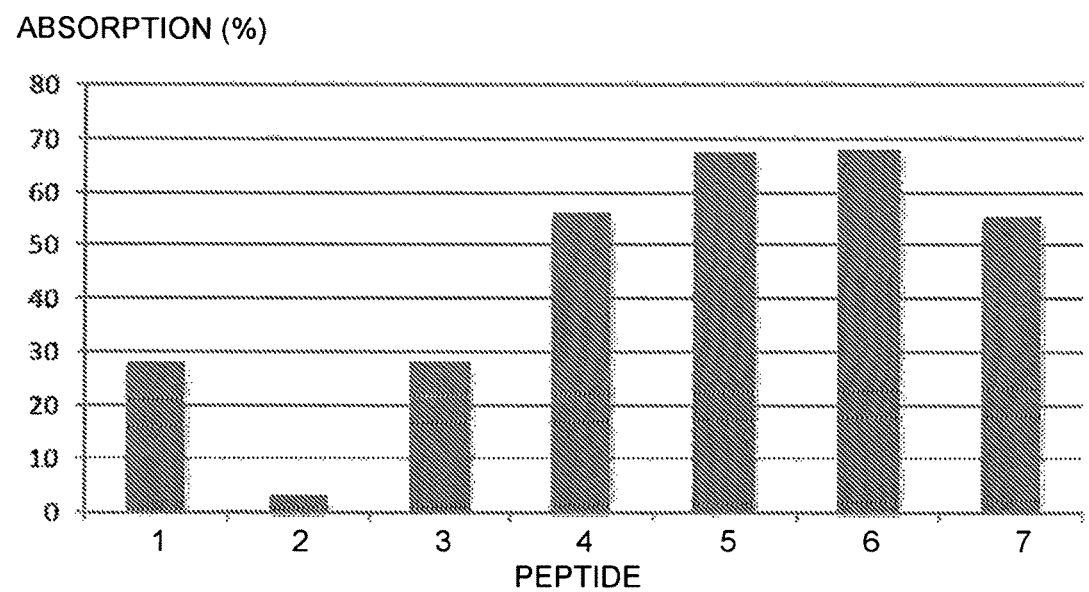
FIG. 3 is a diagram showing percentage of absorbance at 206 nm of different peptide solutions after the incubation with P90 $TiO_2$ particles.

FIG. 3 illustrates the percentage of peptides 1-7 absorbed on $TiO_2$ surfaces (P90) as calculated based on the measured absorbances. The experiment indicated that peptides 5 and 6 bound most to $TiO_2$ P90 followed by peptides 7 and 4.

Figure 4:
FIG. 4 is a diagram showing percentage of absorbance at 206 nm of different peptide solutions after the incubation with P90 $TiO_2$ particles.

FIG. 4 illustrates the percentage of peptides 8-17 absorbed on $TiO_2$ surfaces (P90) as calculated based on the measured absorbances.

Conclusions

The results indicate that the binding between the IP-10 protein and $TiO_2$ surfaces could be related to the beta-hairpin (4:6, EIIATMKKKGEKRC, SEQ ID NO: 19).

Experiment 2: Binding Ability of IP-10 Derived Short Peptide Sequences to Titanium This experiment shows the binding ability of different sequences contained in the IP-10 molecule to titanium dioxide nanoparticles, with the purpose of identifying a putative Ti-binding peptide sequence from IP-10.

Materials and Methods 5 mg of eleven peptides (Table 2) were dissolved with 1 ml of water for molecular biology (Sigma-Aldrich, St. Louis, Mo., USA). Working solutions of the different peptides were diluted further with phosphate buffered saline (PBS) (PAA Laboratories GmbH, Pasching, Austria) to 50 µg/ml. 25 mg of $TiO_2$ (P25 from Degussa and P90 from Sigma-Aldrich) were used for the studies. Briefly, 250 µl of peptide solution was incubated with 25 mg of $TiO_2$ powder with different particle size (P25 and P90) in an orbital shaker (IKA Vibrax VXR basic, Staufen, Germany) for 3 h at room temperature. Different controls were used and processed in parallel with the other samples: solutions with peptides alone, PBS alone and P25/P90 in PBS. After this time, all the samples were centrifuged at 13.000×g for 3 min at 20° C. 100 µl of the supernatant solution was carefully collected and placed in a 96-well UV plate and read with Power-Wave™ microplate spectrophotometer from BioTek. Absorbances at 206 nm and also spectrum curves for each sample were collected and analysed.

TABLE 2

IP-10 derived short sequences

| Identification of peptide | Amino acid sequence | SEQ ID NO: |
|---|---|---|
| IP1 | ATMKK | 20 |
| IP2 | TMKKK | 21 |
| IP3 | MKKKG | 22 |
| IP4 | KKKGE | 23 |
| IP5 | KKGEI | 24 |
| IP6 | KGEII | 25 |
| IP7 | GEIIA | 26 |
| IP8 | IATMK | 27 |
| IP9 | IIATM | 28 |
| IP10 | IIATMKKKGEIIAT | 29 |
| IP11 | KKKKK | 30 |

Results

Figure 5:
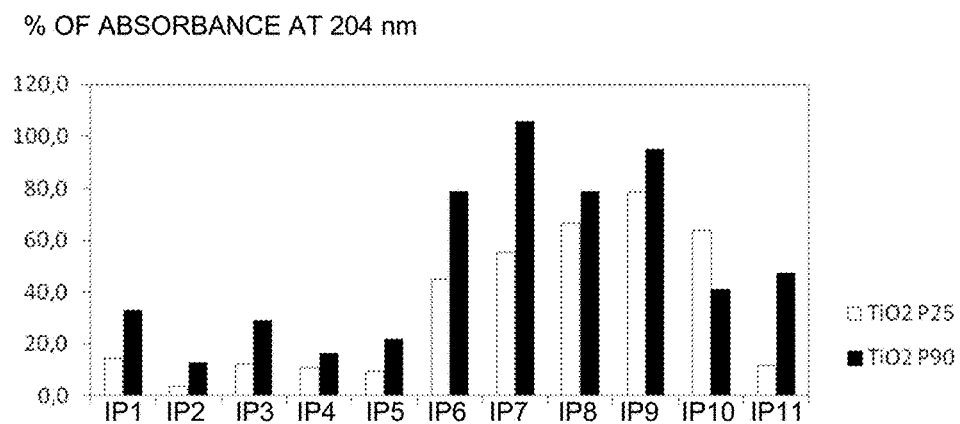
FIG. 5 is a diagram illustrating percentage of absorbance at 206 nm of different peptide solutions after incubation with $TiO_2$ particles of different size, P25 and P90.

FIG. 5 shows the percentage of absorbance at 206 nm of the different peptide solutions after the incubation with $TiO_2$ particles. The reduction of the absorbance at 206 nm in respect of control (peptide solutions alone) clearly indicated a high degree of binding between some of the peptides and $TiO_2$ particles, especially for peptides IP1 to IP5 and IP11 showing 85-96% binding capacity for $TiO_2$ P25. P25 $TiO_2$ particles had a better potential to bind the different peptides as compared to P90 $TiO_2$, except for peptides IP8 and IP10.

Conclusions

The short peptide TMKKK (SEQ ID NO: 21) had a very strong binding, and also peptide sequences ATMKK (SEQ ID NO: 20), MKKKG (SEQ ID NO: 22), KKKGE (SEQ ID NO: 23), KKGEI (SEQ ID NO: 24). Interestingly, these results could be related to the beta-hairpin (4:6, EIIATMK-KKGEKRC (SEQ ID NO: 19)) that is formed in the whole IP-10 protein, where the sequence MKKKGE (SEQ ID NO: 69) is present in the loop, see FIG. 6. Most probably, the amino acids present in the loop are responsible to the binding to titanium in the whole IP-10 molecule. The binding of TMKKK (SEQ ID NO: 21) to the titanium surface is probably through hydrogen bonds between the positively charged peptide sequence at neutral pH and the negatively charged titanium surface.

Experiment 3: Binding Images of IP-10 Derived Short Peptide Sequences to Titanium Foils This experiment shows the binding of fluorescent IP-10 short peptide sequences to titanium foils using fluorescence microscope.

Materials and Methods 5 mg of the different peptides (Table 3), which were labeled with fluorescein isothiocyanate, were dissolved with 1 ml of water with molecular biology degree (Sigma-Aldrich, St. Louis, Mo., USA). Working solutions of the different peptides were diluted further with PBS (PAA Laboratories GmbH, Pasching, Austria) to 50 µg/ml. Briefly, 500 µl of peptide solution was incubated with 8×8 mm Ti foils (Sigma Aldrich, thickness 0.127 mm, 99.7%, cut into 8×8 $mm^2$ samples) in an orbital shaker (IKA Vibrax VXR basic, Staufen, Germany) for 3 h at room temperature. Experiments were run in duplicate.

Ti foils were rinsed twice with PBS to remove unbound labeled peptides. Remaining liquid was allowed to dry and samples were put on microscope slides. Samples were observed with a fluorescence microscope (Leica DM R) using the 488 nm excitation channel to excite fluorescein isothiocyanate-marked peptides. Two images of each surface were taken.

TABLE 3

Fluorescent IP-10 derived short sequences

| Identification of peptide | Amino acid sequence | SEQ ID NO: |
|---|---|---|
| IP10 | TMKKK | 21 |
| IP10a | TMKKKPESCF | 31 |
| IP10b | FCSEPKKKMT | 32 |
| IP10r | PESCF | 33 |

Results

Based on the results of experiment 2, new fluorescent peptides were synthesized:
(1) TMKKK (SEQ ID NO: 21), which was the best binding sequence in experiment 2;
(2) TMKKKPESCF (SEQ ID NO: 31), which contains the previous sequence plus a randomized tag sequence to mimic "anything" that can be attached to the peptide, with the purpose of demonstrating that this IP-10 derived short peptide can be used for binding other sequences to the titanium surface;
(3) FCSEPKKKMT (SEQ ID NO: 32), which is the same sequence as (2) but turned;
(4) PESCF (SEQ ID NO: 33), is a control to show that this randomized tag sequence does not bind to titanium by itself.

Figure 7:
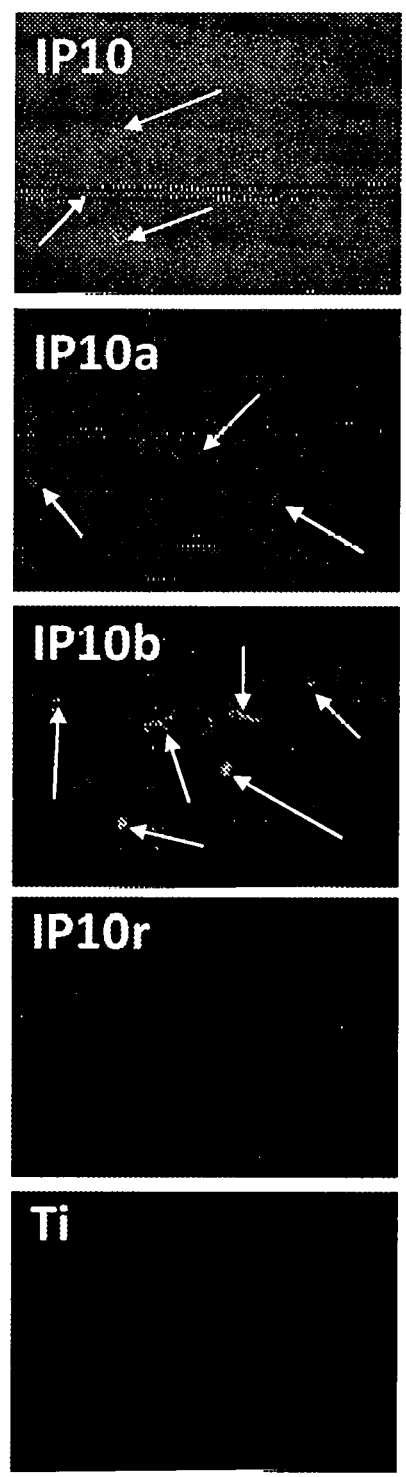
FIG. 7 illustrates fluorescent microscope images of titanium sheets incubated with the different fluorescent IP-10 derived short peptides. The arrows indicate the areas with fluorescent peptide adsorbed on the titanium surface.

FIG. 7 shows that the signal from the different peptides bound to Ti was the highest for IP10 and the lowest for IP10r, while for IP10a and IP10b was lower than for IP10 but higher than for IP10r.

Conclusions

This experiment demonstrates that IP-10 derived short sequences, like TMKKK (SEQ ID NO: 21), can be used to immobilize other molecules to titanium surfaces and thereby form a linker between titanium surfaces and such other molecules, e.g. other peptide sequences.

Experiment 4: In Vitro Effect of Ti-Adsorbed Synthetic Peptides Using IP-10 Sequence as Linker and RGD Sequence as Osteopromotive Signal on MC3T3-E1 Osteoblasts This example shows the effect of binding IP-10 short peptide sequences used as linkers for RGD motif to titanium coins on biocompatibility, cell number and morphology of MC3T3-E1 cells.

Materials and Methods

Peptides

Peptides, see Table 4, were purchased from Eurogentec (AnaSpec peptides, Liege, Belgium). Stock solutions of 5 mg/ml were prepared with ultra-pure $H_2O$ and were further diluted to 50 µg/ml in PBS.

TABLE 4

IP-10 derived short sequences connected to RGD motifs via $G_8$-spacer

| Identification of peptide | Amino acid sequence | SEQ ID NO: |
|---|---|---|
| P1: IP10-RGD | MKKKGEGGGGGGGGRGDS | 34 |
| P2: IP10mut-RGD | MTTTGEGGGGGGGGRGDS | 35 |
| P3: IP10-RGDmut | MKKKGEGGGGGGGGRGES | 36 |
| P4: IP10mut-RGDmu | MTTTGEGGGGGGGGRGES | 37 |

The sequences contained IP-10 short sequence (native and mutated), a spacer of eight glycines and the RGD motif (native and mutated).

Implant Coating with Peptides

Under aseptic conditions, implants were immersed in a 3:7 (v/v) $HNO_3$-DI water solution for 30 min at room temperature. Then, they were rinsed with milliQ water and placed in a covered milliQ water bath for 24 h. Implants were dried with $N_2$ and were placed in a 96-well plates. Then, 200 µl of 50 µg/ml peptide solutions in PBS were added to each implant. Absorption took place for 24 h at 37° C. in a humidified atmosphere. After 24 h peptide solutions were collected and surfaces were washed with 200 µl of PBS and air-dried in order to perform cell experiments. The surfaces were denoted Ti (uncoated Ti), P1 (Ti coated with IP10-RGD), P2 (Ti coated with IP10mut-RGD), P3 (Ti coated with IP10-RGDmut) and P4 (Ti coated with IP10mut-RGDmu).

Cell Culture

MC3T3-E1 cells were routinely cultured at 37° C. in a humidified atmosphere of 5% $CO_2$, and maintained in α-minimum essential medium (α-MEM) supplemented with 10% fetal bovine serum (FBS) and antibiotics (50 IU penicillin/ml and 50 µg streptomycin/ml). $7.0 \times 10^3$ cells were seeded on the peptide-coated implants. Trypan blue stain was used to determine total and viable cell number. The same number of cells was cultured in parallel in plastic culture plates in the experiment. All experiments were performed after 15 passages of the MC3T3-E1 cells.

Cytotoxicity

Lactate dehydrogenase (LDH) activity in the culture media was used as an index of cell death. LDH activity was determined spectrophotometrically after 30 min incubation at 25° C. of 50 µl of culture and 50 µl of the reaction mixture, by measuring the oxidation of NADH at 490 nm in the presence of pyruvate, according to the manufacturers kit instructions (Roche Diagnostics, Mannheim, Germany). Results from all the samples were presented relative to the LDH activity in the medium of cells seeded on uncoated-Ti and cultured for 48 h at 37° C. (low control, 0% of cell death) and on plastic and cultured for 48 h at 37° C. where Triton X-100 was added at 1% (high control, 100% cell death). The percentage of LDH activity was calculated according to the manufacturers protocol.

DNA Quantification

Culture media was removed from wells and plates were frozen at −80° C. until the experiment was carried out. At the day of analysis, 100 µl of distilled water were added to each well. Plates were incubated for 1 hour at room temperature. Again, plates were frozen at −80° C. to lysate cells. Plates were thawed until reaching room temperature and 100 µl of Hoechst 33258 at 20 µg/ml in THE buffer were added. Then, 200 µl aliquots were transferred to 96-well fluorescence plates and a spectrophotometer was set to record fluorescence. Relative fluorescence units were correlated with the cell number using a linear standard curve.

Immunocytochemistry

Cells grown on peptide-coated Ti surfaces were fixed for 15 minutes with 4% formaldehyde in PBS. Cells were washed three times before staining cells with Phalloidin-FITC 50 µg/ml (phalloidin-fluorescein isothiocyanate, stains actin filaments) in Triton X-100 1% in PBS for 30 minutes in the dark. Again, cells were washed with PBS and coin-shaped implants were placed on slides. Finally, a drop of DAPI (4′,6-diamidino-2-phenylindole, stains the nucleus of the cells) was added and cover glasses were mounted on the implants. Two images of each implant were taken with a confocal microscope. Excitation wavelengths of DAPI and Phalloidin-FITC were set at 405 and 488 nm respectively. Fluorescence was captured between 430-480 nm for DAPI and between 500-525 nm for Phalloidin-FITC.

Statistics

All data are presented as mean values±SEM. Differences between groups were assessed by Mann-Whitney-test or by Student t-test depending on their normal distribution. A Kolmogorov-Smirnov test was done to assume parametric or non-parametric distributions for the normality tests. The GraphPad 5.0 program for Windows was used. Results were considered statistically significant at p-values ≤0.05.

Results

Figure 8:
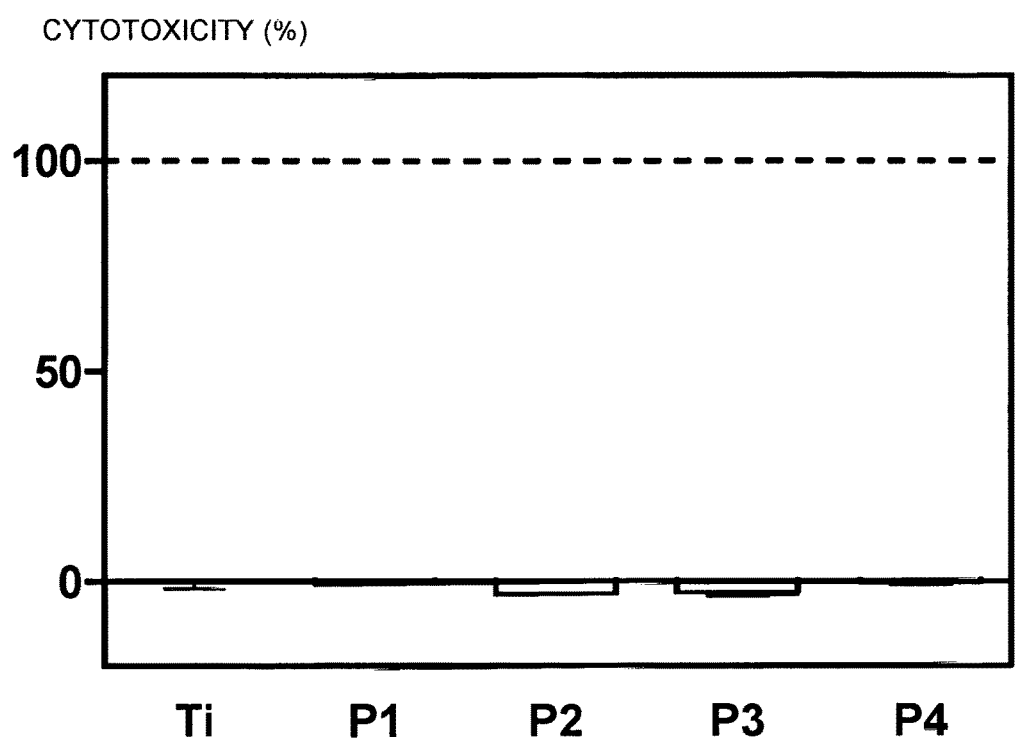
FIG. 8 is a diagram illustrating LDH activity measured from culture media of MC3T3-E1 cells cultured for 48 h on peptide-coated Ti surfaces. High control (100%) was media from cells treated with Triton X-100 1%. Low control (0%) was media from cells seeded on uncoated Ti. No significant differences were found between uncoated-Ti and peptide-coated Ti.

The biocompatibility of peptide-coated Ti coins was evaluated first in vitro by measuring the release of LDH from MC3T3-E1 pre-osteoblasts incubated for 48 hours on the surfaces. FIG. 8 shows that all peptide-coated Ti surfaces were safe for MC3T-E1 cells.

Figure 9:
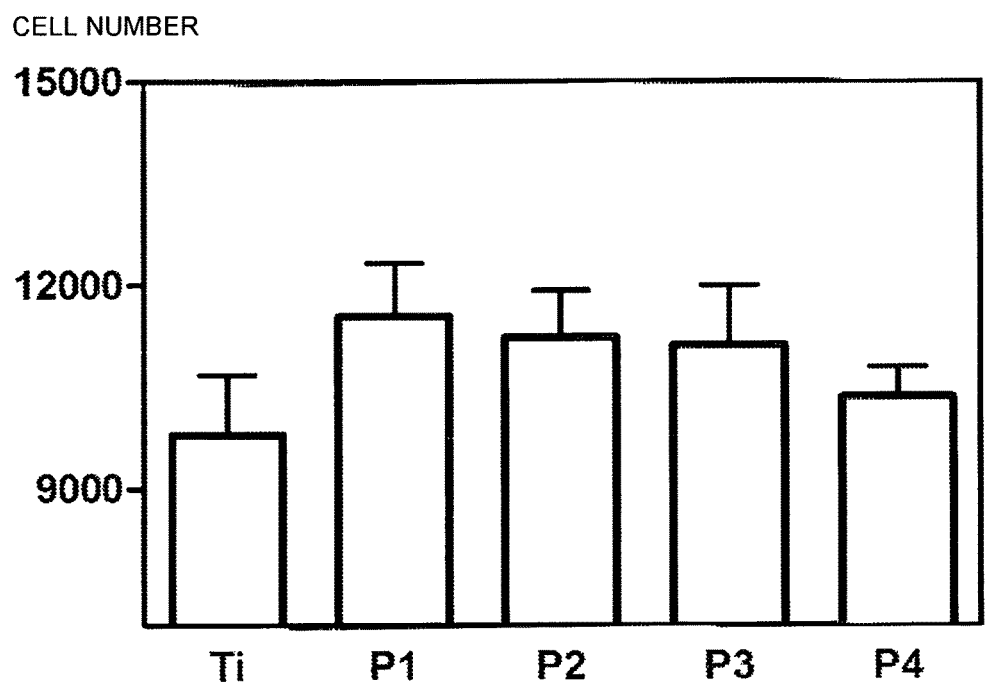
FIG. 9 is a diagram illustrating DNA quantification for MC3T3-E1 cells cultured for 48 h on uncoated Ti and peptide-coated Ti.

A higher number of cells was found on peptide-coated Ti surfaces than on uncoated-Ti (FIG. 9). For peptide-coated groups, P1 group showed the highest number of cells and P4 group the lowest, see FIG. 9.

Figure 10:
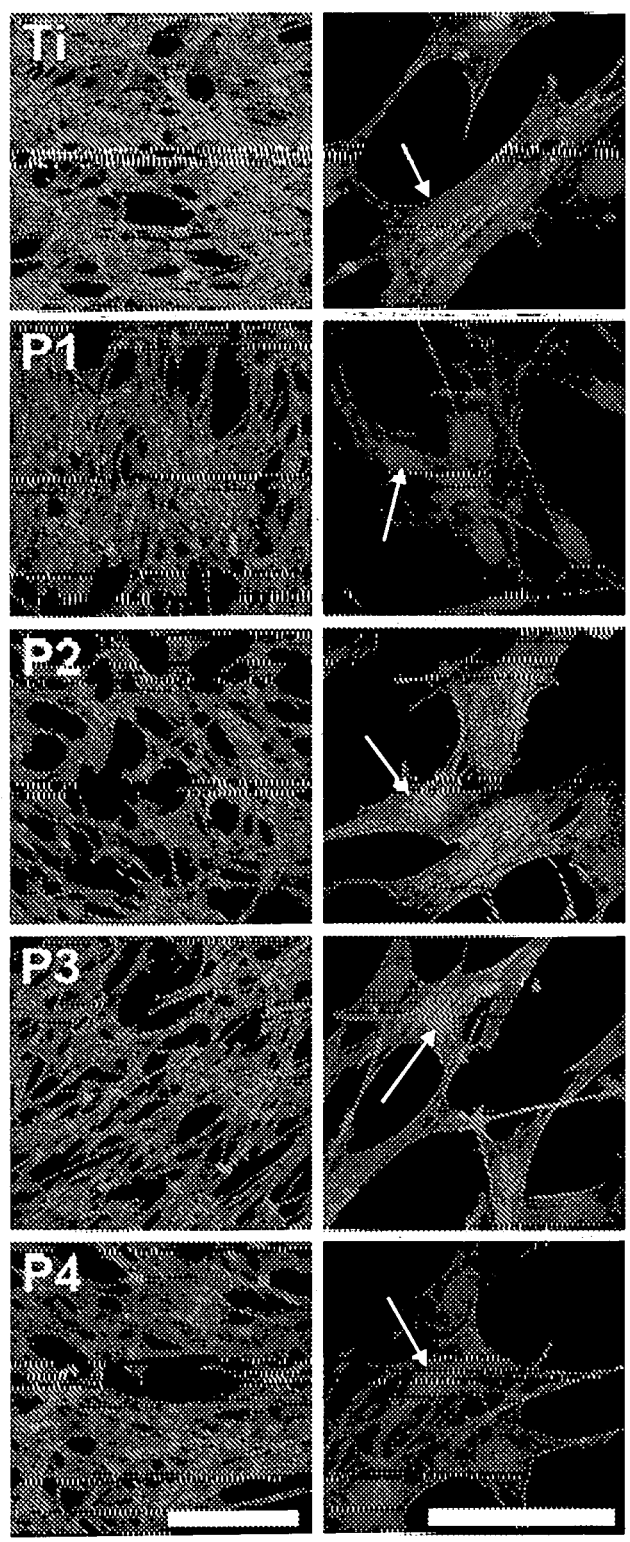
FIG. 10 illustrates images from confocal laser scanning microscopy of MC3T3-E1 cells cultured for 48 hours on uncoated Ti and peptide-coated Ti. Cytoskeleton of cells was stained with Phalloidin-FITC (green) and nuclei with DAPI (blue). Bar scale=100 μm (left) and 50 μm (right). The arrows indicate MC3T3-E1 cells.

Confocal images show (FIG. 10) that MC3T3-E1 cells had the typical osteoblastic morphology on the different surfaces. Several cell-to-cell and cell-to-surfaces contacts were observed in all groups.

Conclusions

This experiment demonstrated that coating titanium coins with IP-10 short sequences (used as linkers for RGD peptides) by physisorption is a feasible approach, showing a biological effect in vitro in MC3T3-E1 cells. Peptide-coating of Ti was safe for MC3T3-E1 pre-osteoblasts and permitted the acquisition of the typical osteoblastic morphology.

Importantly, cell number determination showed that titanium surfaces coated with P1 permitted the highest number of cells than the other peptide sequences and control surface without coating, followed by the P2 and P3 (single mutants for either IP-10 short sequence or RGD) and lastly the double mutant peptide sequence (for IP-10 short sequence and RGD).

Experiment 5: In Vitro Effect of Ti-Adsorbed Synthetic Peptides Using IP-10 Sequence as Linker and RGD Sequence on Integrin Expression in MC3T3-E1 Osteoblasts This experiment shows the effect of binding IP-10 short peptide sequences (used as linkers for RGD motif) to titanium coins on integrin expression in MC3T3-E1 cells, as RGD is a well-known recognition sequence for integrins.

The aim was to evaluate the expression over time of different genes involved in cell adhesion of osteoblastic cells seeded on Ti surfaces coated with the synthetic peptides designed, according to the requirements of current standards (i.a. ISO 10993-5: Biological Evaluation of Medical Devices). The bioactivity was assessed through the gene expression analysis of integrin α8, integrin β3 and collagen type-I after 24 and 72 hours of cell culture. Then, integrin β3 production was evaluated using specific antibodies and confocal microscopy.

Materials and Methods

Peptides

The same peptides as in experiment 4 was used. Stock solutions of 5 mg/ml were prepared with ultra-pure $H_2O$ and were further diluted to 50 μg/ml in PBS.

Implant Coating with Peptides

Under aseptic conditions, implants were immersed in a 3:7 (v/v) $HNO_3$-DI water solution for 30 min at room temperature. Then, they were rinsed with milliQ water and placed in a covered milliQ water bath for 24 h. Implants were dried with $N_2$ and were placed in a 96-well plates. Then, 200 μl of 50 μg/ml peptide solutions in PBS were added to each implant. Adsorption took place for 24 h at 37° C. in a humidified atmosphere. After 24 h peptide solutions were collected and surfaces were washed with 200 μl of PBS and air-dried in order to perform in vitro experiments.

Cell Culture

MC3T3-E1 cells were routinely cultured at 37° C. in a humidified atmosphere of 5% $CO_2$, and maintained in α-MEM supplemented with 10% FBS and antibiotics (50 IU penicillin/ml and 50 μg streptomycin/ml). $7.0 \times 10^3$ cells were seeded on the peptide-coated implants. Trypan blue stain was used to determine total and viable cell number. The same number of cells was cultured in parallel in plastic culture plates in the experiment. All experiments were performed after 4 passages of the MC3T3-E1 cells.

Immunocytochemistry

Cells grown for 24 and 72 h on the surfaces were fixed for 15 min with 4% formaldehyde in PBS at room temperature. Cells were incubated with 0.1% Triton X-100 for 5 min, 1% bovine serum albumin for 30 min and then with anti-integrin beta-3 antibody for 1 h at 1:50 dilution in PBS. Then, a Cy3-conjugated goat anti-rabbit IgG was used as secondary antibody for 1.5 h at 1:200 dilution in PBS. For actin cytoskeleton visualization, cells were stained with phalloidin-FITC 5 μg/mL in PBS for 30 min. Cells were washed with PBS and coin-shaped samples were placed on slides. Finally, a drop of Fluoroshield with DAPI was added and cover glasses were mounted on the samples. Two samples of each group were used to perform the experiment and two images of each sample were taken with the confocal microscope (Leica DMI 4000B equipped with Leica TCS SPE laser system).

RNA Isolation and Real-Time RT-PCR Analysis

Total RNA was isolated using Tripure, according to the manufacturer's protocol. Total RNA was quantified at 260 nm using a Nanodrop spectrophotometer. The same amount of RNA (100 ng) was reverse transcribed to cDNA at 42° C. for 60 min using High Capacity RNA-to-cDNA kit, according to the protocol of the supplier. Aliquots of each cDNA were frozen (−20° C.) until the PCR reactions were carried out.

Real-time PCR was performed in the Lightcycler 480® using SYBR green detection. Real time PCR was done for two reference genes (18S rRNA and glyceraldehyde-3-phosphate dehydrogenase (Gapdh)) and target genes (collagen type I (Col1a1)), and integrins α8 and β3 (Itga8 and Itgb3). The primer sequences were designed using the NCBI primer designing tool and are detailed in Table 5.

Each reaction contained 7 μl Lightcycler-FastStart DNA MasterPLUS SYBR Green I (containing Fast Start Taq polymerase, reaction buffer, dNTPs mix, SYBRGreen I dye and $MgCl_2$), 0.5 μM of each, the sense and the antisense specific primers and 3 μl of the cDNA dilution in a final volume of 10 μl. The amplification program consisted of a preincubation step for denaturation of the template cDNA (10 min 95° C.), followed by 45 cycles consisting of a denaturation step (10 s 95° C.), an annealing step (10 s 60° C.) and an extension step (10 s 72° C.). After each cycle, fluorescence was measured at 72° C. (λex 470 nm, λem 530 nm). A negative control without cDNA template was run in each assay.

Real-time efficiencies (E) were calculated from the given slopes in the LightCycler 480 software using serial dilutions, showing all the investigated transcripts high real-time PCR efficiency rates, and high linearity when different concentrations were used. PCR products were subjected to a melting curve analysis on the LightCycler and subsequently 2% agarose/TAE gel electrophoresis to confirm amplification specificity, Tm and amplicon size, respectively.

All samples were normalized by the geometric mean of the expression levels of 18S rRNA and Gapdh and fold changes were related to day 1 of culture using the mathematical model described by Pfaffl, A new mathematical model for relative quantification in real-time RT-PCR, *Nucleic Acids Research* 2001, 29: e45:

$$\text{Ratio} = \frac{E_{target}^{\Delta Cp_{target}(mean\ Ti\ 24\ h-sample)}}{E_{reference}^{\Delta Cp_{target}(mean\ Ti\ 24\ h-sample)}}$$

where Cp is the crossing point of the reaction amplification curve as determined by the LightCycler 480 software.

TABLE 5

Primer sequences used for real-time RT-PCR analysis

| Gene | Primer sequence | SEQ ID NO: |
|---|---|---|
| 18S rRNA | S 5'-GTAACCCGTTGAACCCCATT-3' | 38 |
|  | A 5'-CCATCCAATCGGTAGTAGCG-3' | 39 |
| Gapdh | S 5'-ACCCAGAAGACTGTGGATGG-3' | 40 |
|  | A 5'-CACATTGGGGGTAGGAACAC-3' | 41 |
| Col1a1 | S 5'-AGAGCATGACCGATGGATTC-3' | 42 |
|  | A 5'-CCTTCTTGAGGTTGCCAGTC-3' | 43 |
| Itga8 | S 5'-TCGCCTGGGAGGAGGCGAAA-3' | 44 |
|  | A 5'-TCTTAACCGCTGTGCTCCCCG-3' | 45 |
| Itgb3 | S 5'-AGGGGAGATGTGTTCCGGCCA-3' | 46 |
|  | A 5'-ACACACAGCTGCCGCACTCG-3' | 47 |

S = sense
A = anti-sense

Statistics

All data are presented as mean values±SEM. Differences between groups were assessed by Mann-Whitney-test or by Student t-test depending on their normal distribution. A Kolmogorov-Smirnov test was done to assume parametric or non-parametric distributions for the normality tests. The GraphPad 5.0 program for Windows was used. Results were considered statistically significant at p-values ≤0.05.

Results

Figure 11:
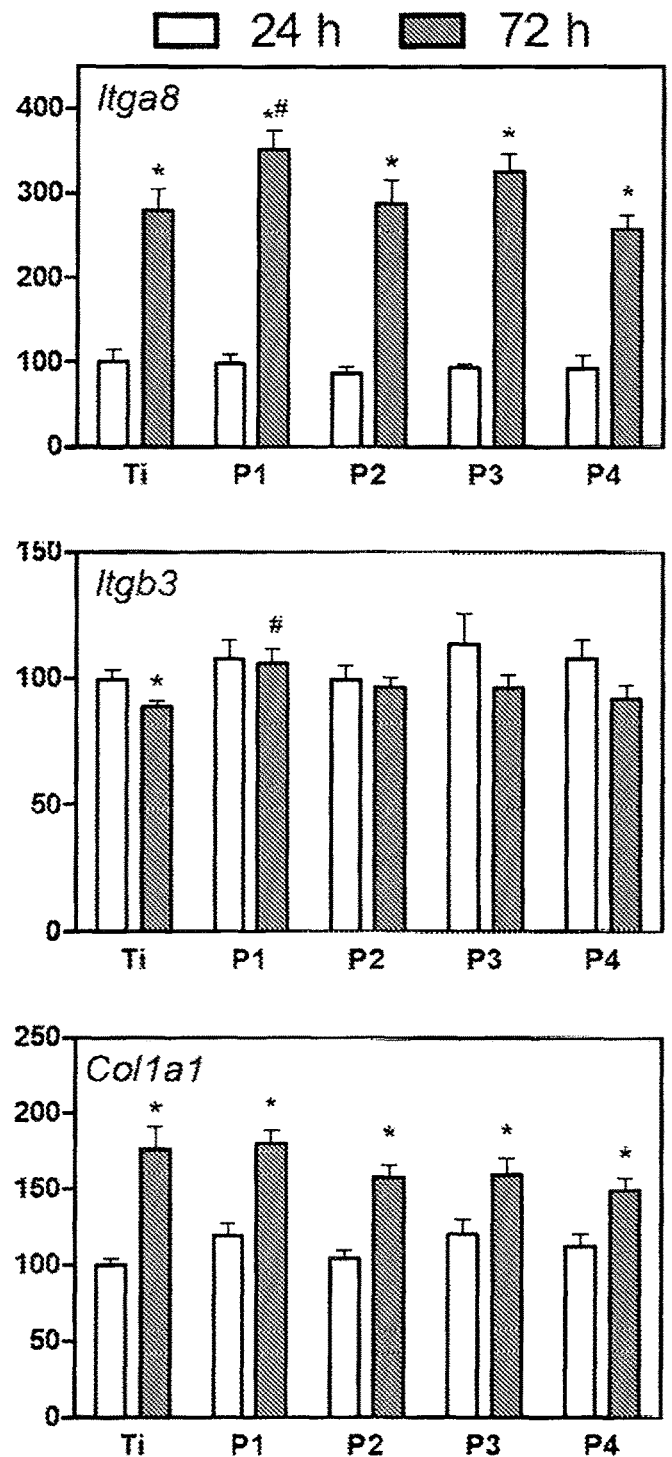
FIG. 11 illustrates gene expression levels of Integrin α8 (Itga8), integrin β3 (Itgb3) and collagen type-I (Col1a1). Data represent fold changes of target genes normalized to beta-actin and GAPDH (reference genes) expressed relative to cells on uncoated Ti after 24 h that were set at 100%. Values represent the mean±SEM (n=6). Significant differences were assessed by Student t-test: (*) $p \leq 0.05$ versus uncoated Ti after 24 hours (Ti 24 h); (#) $p \leq 0.05$ versus uncoated Ti after 72 hours (Ti 72 h).

FIG. 11 shows that the expression of Itga8 and Itgb3 increased on P1-coated surfaces compared with uncoated surfaces after 72 h on cell culture. Moreover, the expression of Itga8 and Col1a1 increased on all surfaces after 72 h, compared with uncoated Ti after 24 h, while the expression of Itgb3 did not.

Figure 12:
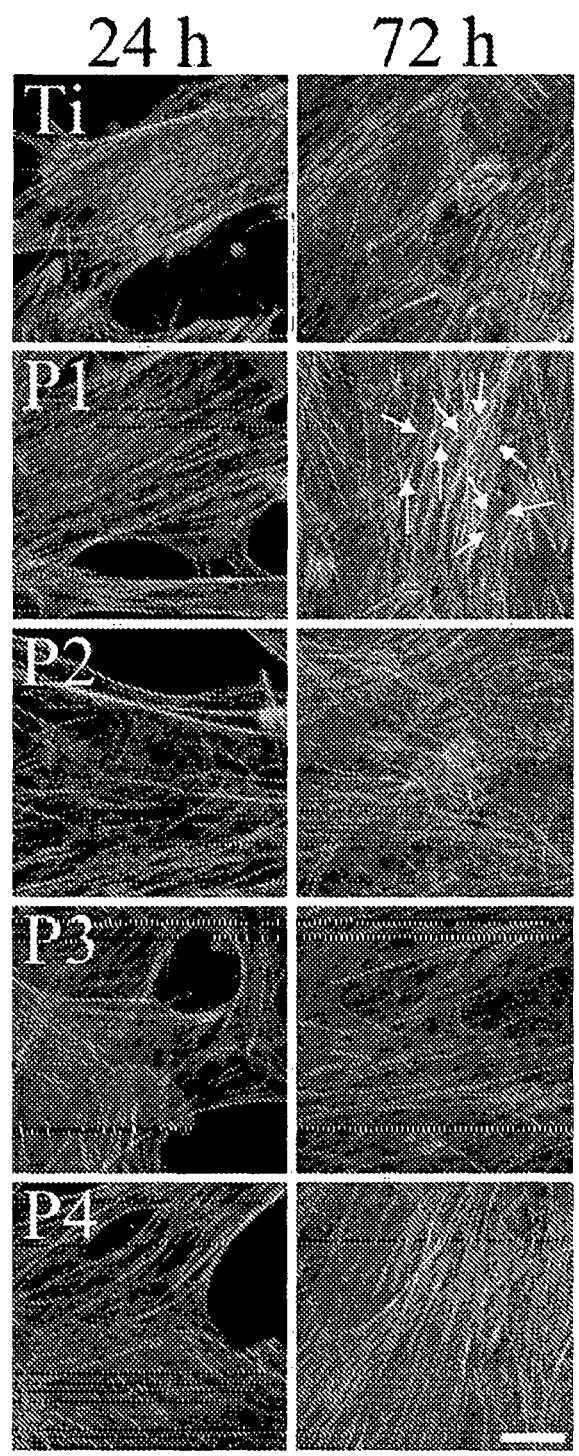
FIG. 12 illustrates images from confocal laser scanning microscopy of MC3T3-E1 cells cultured for 24 and 72 hours on uncoated-Ti and peptide-coated Ti. Cytoskeleton of cells was stained with Phalloidin-FITC; nuclei with DAPI; and specific antibodies were used against integrin β3. White arrows indicate integrin β3 staining. Bar scale=10 μm.

FIG. 12 shows that MC3T3-E1 cells had the typical osteoblastic morphology on the different surfaces. P1-coated surfaces and uncoated-Ti allowed integrin β3 visualization after 72 h of culture while on P2-, P3- and P4-coated surfaces no clear staining was observed. P1-coated surfaces showed the highest integrin β3 staining from all surfaces after 72 h. Noteworthy, P3-coated surfaces showed integrin β3 signal after 24 h of culture, although it disappeared after 72 hours.

Conclusions

This experiment demonstrated that P1-coated surfaces (with IP-10 short sequence and RGD motif) allowed an increased gene expression of integrin α8 and integrin β3 compared with uncoated-Ti. P1-coated surfaces allowed specific anti-integrin β3 staining while the other peptide-coatings did not. This demonstrates that IP-10 short sequence can be used to link target sequences (like RGD) to the implant surface to exert their biological effect on the cells.

Experiment 6: Binding of IP-10 to Different Materials

This experiment was conducted to investigate the how much IP-10 various material and metals could bind.

Materials and Methods 20 mg of each material was incubated with 500 µml of human serum comprising IP-10 (12 ng/ml) for 3 h at room temperature and samples were vortexed four times during the incubation. The materials was kept frozen (−20° C.) until IP-10 analysis. The amount of IP-10 in the supernatant following centrifugation at 10 000×g, 3 min was determined by ELISA (R&D Systems).

The following materials were tested in this experiment:

Gray Granule, diameter ~1 mm, 99.97%, >80% sponge form, Hereford.
White Granule, heat treated Gray Granule (900° C. 3 h).
Grey Powder, sifted Grey Granule, diameter <0.075 mm.
White Powder, sifted White Granule, diameter <0.2 mm.
Titanium, diameter <45 µm, 99.98%, catalog number 366994, Sigma Aldrich.
Ti(IV)Ox, rutile, diameter <5 µm, 99.9+%, catalog number 224227, Sigma Aldrich.
TiDiOx, diameter 21 nm, product number P 25, Aerosil Evonic Ind.
TiDiOx, anatase, Sachtleben*.
TiIIOx, diameter <45 µm, 99.9%, catalog number 48, 104-1, Sigma Aldrich.
TiOx (painting), OVKC, Alfort & Cronholm.
Titaniumcarbid, diameter <2 µm, Roth.
Stainless steel, diameter <45 µm, 99.9%, item number SS-103, Atlantic Equipment Engineers.
Vanadium, diameter <45 µm, 99.5%, catalog number 262956, Sigma Aldrich.
Tantalum, <45 µm, 99.9%, catalog number 262846, Sigma Aldrich.
Zirconium(IV)Ox, diameter <5 µm, 99%, catalog number 230693, Sigma Aldrish.
Niobium(V)Ox, diameter <45 µm, 99.9%, catalog number 208515, Sigma Aldrich.
Copper(I)Ox, diameter <5 µm, 97%, catalog number 208825, Sigma Aldrich.
Iron(II,III)Ox, diameter <5 µm, 98%, catalog number 310069, Sigma Aldrich.
Cobalt(II)Ox, diameter <45 µm, catalog number 343153, Sigma Aldrich.
Cobalt(II,III)Ox, diameter <10 µm, catalog number 221643, Sigma Aldrich.
Diamond, diameter 1 µm, 99.9%, catalog number 483591, Sigma Aldrich.
Hydroxyapatite, diameter 200 nm, catalog number 289396, Sigma Aldrich.
Chromium(III)Ox, diameter <100 nm, 99%, catalog number 634239, Sigma Aldrich.
Bismuth(III)Ox, diameter <100 nm, 99.9%, catalog number 637017, Sigma Aldrich.
MagnesiumOx, diameter <50 nm, catalog number 549649, Sigma Aldrich.
Carbon, diameter <50 nm, 99%, catalog number 633100, Sigma Aldrich.
Silicondioxide, diameter 10-20 nm, 99.5%, catalog number 637238, Sigma Aldrich.
Aluminium oxide, diameter <10 µm, 99.5%, catalog number 265497, Sigma Aldrich.
Aluminium oxide, diameter <50 nm, catalog number 2544833, Sigma Aldrich.
Silver(I)Ox, >99.0%, catalog number 85260, Sigma Aldrich*.
Gold(III)Ox, 85-86%, catalog number 334057, Sigma Aldrich*.
Gallium(III)Ox, 99%, catalog number 10427, Sigma Aldrich*.
HafniumOx, 98%, catalog number 202117, Sigma Aldrich*.
ZincOx, >99.0%, catalog number 96484, Sigma Aldrich*.
Calciumphosphate, >96.0%, catalog number 21218, Sigma Aldrich*.
Manganese(II,III)Ox, 97%, catalog number 377473, Sigma Aldrich*.
Nickel(II)Ox, diameter <10 µm, catalog number 244031, Sigma Aldrich.
PVDF membrane.
*particle size not known/specified Results The binding of IP-10 to the tested materials is illustrated in FIG. 13. In addition to titanium, the material binding most IP-10 was vanadium, tantalum, zirconium, niobium, diamond, chromium, silicon dioxide, silver oxide, hafnium oxide and gold oxide.

Conclusions

IP-10 seemed to bind well to materials that are generally regarded as being biocompatible.

Experiment 7: Binding Ability of IP-10 Derived Short Peptide Sequences to Titanium Dioxide, Silicon Oxide and Magnesium Oxide This example shows the binding ability of different sequences contained in the IP-10 molecule to titanium dioxide nanoparticles, with the purpose of identifying a putative Ti-binding peptide sequence. Results are compared to the binding to silicon dioxide and magnesium oxide.

Materials and Methods

Lyophilized peptides were dissolved with water (Sigma, molecular biology degree) to a concentration of 5 mg/ml (Table 6). Working solutions of the different peptides were diluted further with PBS (PAA laboratories) to 50 µg/ml. 25 mg of $TiO_2$ (Titanium(IV) oxide nanopowder, 21 nm particle size, catalog number 718467, Sigma-Aldrich), $SiO_2$ (Silicon dioxide nanopowder, 10-20 nm particle size, catalog number 63/238, Sigma-aldrich), MgO (Magnesium oxide nanopowder, <50 nm particle size, catalog number 549649, Sigma-Aldrich) were used for the studies. Briefly, 250 µl of peptide solution containing 50 µg/ml was incubated with 25 mg of the materials in an orbital shaker for 3 h at room temperature. Different controls were used and processed in parallel with the other samples: solutions with peptides alone, PBS alone and $TiO_2$/$SiO_2$/MgO in PBS. After this time, all the samples were centrifuged at 13.000×g for 3 min at 20° C. 100 µl of the supernatant solution was carefully collected and placed in a 96-well UV plate and read with PowerWave™ microplate spectrophotometer from BioTek. Absorbances at 206 nm and also spectrum curves for each sample were collected and analyzed.

TABLE 6

IP-10 derived short sequences used in the binding studies

| Identification of peptide | Amino acid sequence | SEQ ID NO: |
|---|---|---|
| IP9 (1) | IIATM | 28 |
| IP8 (2) | IATMK | 27 |
| IP1 (3) | ATMKK | 29 |
| IP2 (4) | TMKKK | 21 |
| IP3 (5) | MKKKG | 22 |
| IP4 (6) | KKKGE | 23 |
| IPA (7) | KKGEK | 48 |
| IPB (8) | KGEKR | 49 |

TABLE 6-continued

IP-10 derived short sequences used in the binding studies

| Identification of peptide | Amino acid sequence | SEQ ID NO: |
|---|---|---|
| IPC (9) | GEKRC | 50 |
| IPD (10) | EKRCL | 51 |
| IPE (11) | KRCLN | 52 |
| IPF (12) | RCLNP | 53 |
| IPG (13) | CLNPE | 54 |
| IPH (14) | LNPES | 55 |

Figure 14:
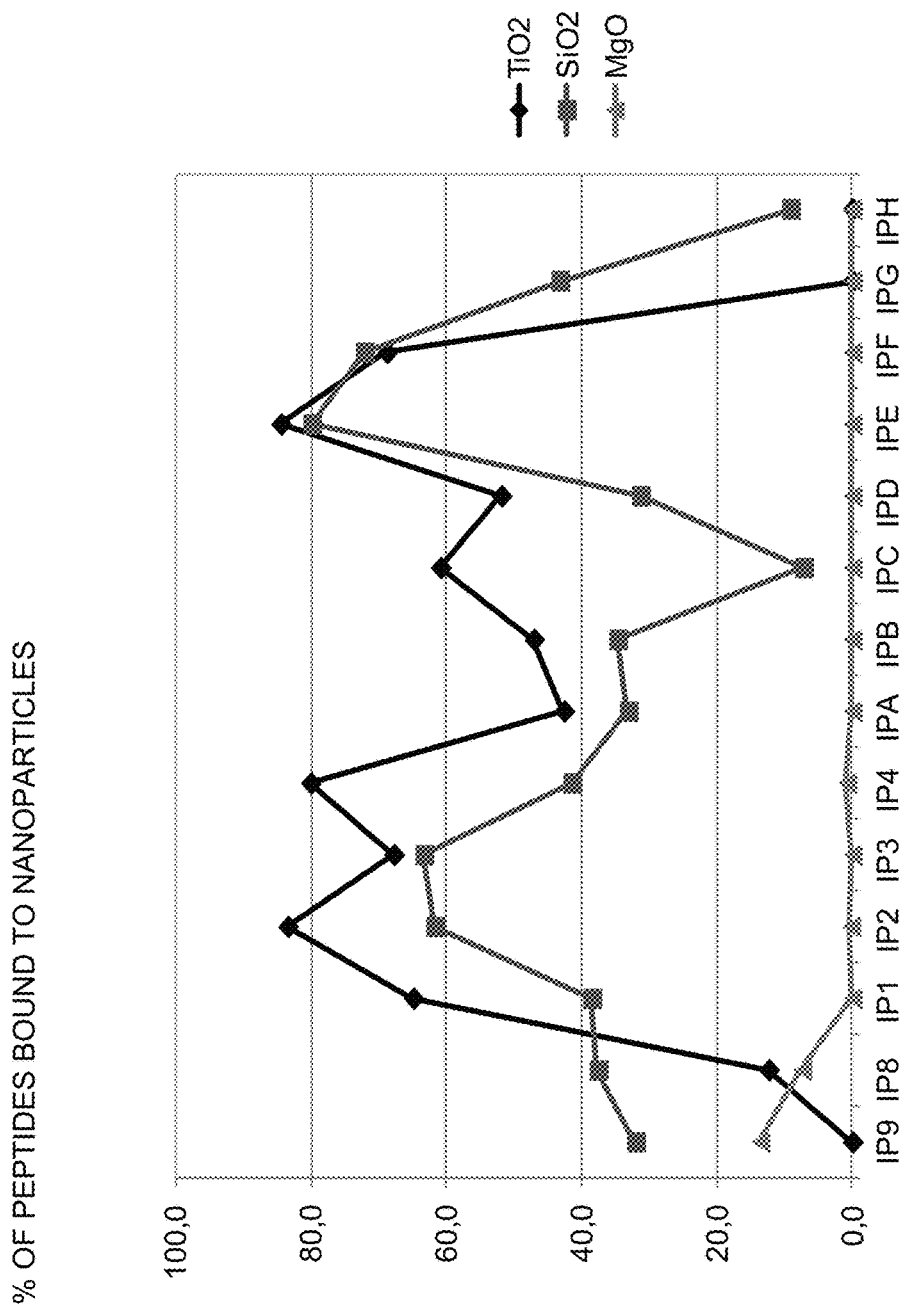
FIG. 14 is a diagram illustrating the percentage of peptides bound to the different nanoparticles after 3 h incubation at room temperature. Binding of the peptides was measured by reading the absorbance at 206 nm.

FIG. 14 shows % of peptides bound to the different nanoparticles of $TiO_2$, $SiO_2$ and MgO depending on the sequence. The reduction of the absorbance at 206 nm in respect of control (peptide solutions alone in PBS), after correction of absorbances with the readings of PBS alone and nanoparticles in PBS without peptides, clearly indicated a high degree of binding between some of the peptides and $TiO_2$ and $SiO_2$ particles, but not for MgO. $TiO_2$ nanoparticles showed a similar but higher binding than $SiO_2$ particles.

The peptides with higher binding to $TiO_2$ nanoparticles were TMKKK (SEQ ID NO: 21), MKKKG (SEQ ID NO: 22), KKKGE (SEQ ID NO: 23) (already identified in Example 2), which are contained in the beta-hairpin (4:6, EIIATMKKKGEKRC (SEQ ID NO: 19)) that is formed in the IP-10 protein, and where these sequences are present in the loop. We have also newly identified KRCLN (SEQ ID NO: 52) and RCLNP (SEQ ID NO: 53) as new peptide sequences binding to $TiO_2$ and $SiO_2$.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An isolated combined surface-binding peptide consisting of at least two surface-binding peptides, wherein each of said at least two surface-binding peptides consists of N consecutive amino acids of an extended beta-hairpin motif EIIATMKKKGEKRCLNP (SEQ ID NO: 57) in interferon gamma-induced protein 10 (IP-10), wherein N=5-17, with the provisos that none of said surface-binding peptides are GEKRCL (SEQ ID NO: 65), and the sequence of said combined surface-binding peptide is different from any consecutive amino acid sequence portion of IP-10.

2. The isolated combined surface-binding peptide according to claim 1, wherein each of said at least two surface-binding peptides consists of N consecutive amino acids of the beta-hairpin motif EIIATMKKKGEKRC (SEQ ID NO: 19) in IP-10, wherein N=5-14.

3. The isolated combined surface-binding peptide according to claim 2, wherein each of said at least two surface-binding peptides consists of N consecutive amino acids of ATMKKKGEKRC (SEQ ID: NO: 56), wherein N=5-11.

4. The isolated combined surface-binding peptide according to claim 1, wherein each of said at least two surface-binding peptides consists of N consecutive amino acids of ATMKKKGEKRCLNP (SEQ ID: NO: 58), wherein N=5-14.

5. The isolated combined surface-binding peptide according to claim 1, wherein each of said at least two surface-binding peptides consists of an amino acid sequence selected from the group consisting of:

ATMKK; (SEQ ID NO: 20)

TMKKK; (SEQ ID NO: 21)

MKKKG; (SEQ ID NO: 22)

KKKGE; (SEQ ID NO: 23)

KKGEK; (SEQ ID NO: 48)

KGEKR; (SEQ ID NO: 49)

GEKRC; (SEQ ID NO: 50)

-continued

EKRCL; (SEQ ID NO: 51)

KRCLN; (SEQ ID NO: 52)
and

RCLNP. (SEQ ID NO: 53)

6. A surface-binding molecule consisting of a surface-binding peptide directly linked or linked through a spacer or linker to a heterologous molecule of interest, wherein said surface-binding peptide is selected from the group consisting of:
  (i) a surface-binding peptide consisting of N consecutive amino acids of an extended beta-hairpin motif EIIATMKKKGEKRCLNP (SEQ ID NO: 57) in interferon gamma-induced protein 10 (IP-10), wherein N=5-17, with the proviso that surface-binding peptide is not GEKRCL (SEQ ID NO: 65); and
  (ii) an isolated combined surface-binding peptide according to claim 1.

7. The surface-binding molecule according to claim 6, wherein the linked surface-binding peptide is selected from the group consisting of:
  a surface-binding peptide comprising the amino acid sequence of ATMKK (SEQ ID NO: 20);
  a surface-binding peptide comprising the amino acid sequence of TMKKK (SEQ ID NO: 21);
  a surface-binding peptide comprising the amino acid sequence of MKKKG (SEQ ID NO: 22);
  a surface-binding peptide comprising the amino acid sequence of KKKGE (SEQ ID NO: 23);
  a surface-binding peptide comprising the amino acid sequence of KRCLN (SEQ ID NO: 52); and
  a surface-binding peptide comprising the amino acid sequence of RCLNP (SEQ ID NO: 53).

8. The surface-binding molecule according to claim 6, wherein the surface-binding peptide is selected from the group consisting of:
  a surface-binding peptide consisting of the amino acid sequence of ATMKK (SEQ ID NO: 20);
  a surface-binding peptide consisting of the amino acid sequence of TMKKK (SEQ ID NO: 21);
  a surface-binding peptide consisting of the amino acid sequence of MKKKG (SEQ ID NO: 22);
  a surface-binding peptide consisting of the amino acid sequence of KKKGE (SEQ ID NO: 23);
  a surface-binding peptide consisting of the amino acid sequence of KRCLN (SEQ ID NO: 52); and
  a surface-binding peptide consisting of the amino acid sequence of RCLNP (SEQ ID NO: 53).

9. The surface-binding molecule according to claim 6, wherein said surface-binding peptide is linked to said heterologous molecule of interest through a spacer or a linker.

10. The surface-binding molecule according to claim 6, wherein said heterologous molecule of interest is selected from the group consisting of markers, cell adhesion/attachment molecules, extracellular matrix molecules, basal laminal molecules, anti-inflammatory molecules, antimicrobial molecules, growth factors, growth inhibitors, chemotherapeutic agents, enzymes, antibodies, DNA molecules, RNA molecules, receptors and ligands.

11. An artificial surface comprising a surface of a biocompatible material to which a surface-binding peptide is bound, wherein said surface-binding peptide consists of N consecutive amino acids of an extended beta-hairpin motif EIIATMKKKGEKRCLNP (SEQ ID NO: 57) in interferon gamma-induced protein 10 (IP-10), wherein N=5-17, with the proviso that said isolated surface-binding peptide is not GEKRCL (SEQ ID NO: 65).

12. The artificial surface according to claim 11, wherein said biocompatible material is selected from the group consisting of a metal of group 4 or 5 of the periodic table of the elements, an oxide of a metal of group 4 or 5 of the periodic table of the elements, silver, an oxide of silver, gold, an oxide of gold, and an oxide of silicon.

13. The artificial surface according to claim 12, wherein said biocompatible material is selected from the group consisting of titanium, an oxide of titanium, zirconium, an oxide of zirconium, hafnium, an oxide of hafnium, niobium, an oxide of niobium, tantalum, and an oxide of tantalum.

14. The artificial surface according to claim 13, wherein said biocompatible material is titanium or an oxide of titanium.

15. The artificial surface according to claim 11, wherein said surface is a surface of an implant or of an implantable medical device.

16. An artificial surface comprising a surface of a biocompatible material to which a surface-binding molecule according to claim 6 is bound, wherein said heterologous molecule of interest is attached to said surface through binding of said surface-binding peptide to said surface.

17. The artificial surface according to claim 16, wherein said biocompatible material is selected from the group consisting of a metal of group 4 or 5 of the periodic table of the elements, an oxide of a metal of group 4 or 5 of the periodic table of the elements, silver, an oxide of silver, gold, an oxide of gold, and an oxide of silicon.

18. The artificial surface according to claim 17, wherein said biocompatible material is selected from the group consisting of titanium, an oxide of titanium, zirconium, an oxide of zirconium, hafnium, an oxide of hafnium, niobium, an oxide of niobium, tantalum, and an oxide of tantalum.

19. The artificial surface according to claim 18, wherein said biocompatible material is titanium or an oxide of titanium.

20. The artificial surface according to claim 16, wherein said surface is a surface of an implant or of an implantable medical device.

21. A method of producing an artificial surface comprising binding a surface-binding peptide to a surface of a biocompatible material, wherein said surface-binding peptide consists of N consecutive amino acids of an extended beta-hairpin motif EIIATMKKKGEKRCLNP (SEQ ID NO: 57) in interferon gamma-induced protein 10 (IP-10), wherein N=5-17, with the proviso that said isolated surface-binding peptide is not GEKRCL (SEQ ID NO: 65).

22. A method of producing an artificial surface comprising binding a surface-binding molecule according to claim 6 to a surface of a biocompatible material, wherein said heterologous molecule of interest becomes attached to said surface through binding of said surface-binding peptide to said surface.

* * * * *

UNITED STATES PATENT AND TRADEMARK OFFICE
CERTIFICATE OF CORRECTION

PATENT NO.         : 9,957,311 B2
APPLICATION NO.    : 15/106190
DATED              : May 1, 2018
INVENTOR(S)        : Lars Bruce et al.

It is certified that error appears in the above-identified patent and that said Letters Patent is hereby corrected as shown below:

On the Title Page

Item "(30) Foreign Application Priority Data", change "1351541" to --1351541-6--.

Signed and Sealed this
Twenty-first Day of August, 2018

Andrei Iancu
*Director of the United States Patent and Trademark Office*